United States Patent [19]

Nishikido et al.

[11] Patent Number: 4,616,081
[45] Date of Patent: Oct. 7, 1986

[54] CEPHALOSPORIN COMPOUNDS

[75] Inventors: Joji Nishikido; Eiji Kodama; Chisei Shibuya, all of Fuji, Japan

[73] Assignee: Asahi Kasei Kogyo Kabushiki Kaisha, Japan

[21] Appl. No.: 511,183

[22] Filed: Jul. 6, 1983

[30] Foreign Application Priority Data

| Jul. 7, 1982 | [JP] | Japan | 57-116945 |
| Oct. 8, 1982 | [JP] | Japan | 57-176048 |
| Jan. 11, 1983 | [JP] | Japan | 58-1720 |
| Apr. 13, 1983 | [JP] | Japan | 58-63750 |
| Apr. 18, 1983 | [JP] | Japan | 58-66960 |
| Apr. 18, 1983 | [JP] | Japan | 58-66961 |

[51] Int. Cl.$^4$ .................. C07D 501/36; A61K 31/545
[52] U.S. Cl. ...................... 540/222; 544/90; 544/253; 540/221; 540/225; 540/227
[58] Field of Search ............. 544/16, 22, 258, 25, 544/27, 21; 424/246; 514/202, 203, 204, 206

[56] References Cited

U.S. PATENT DOCUMENTS

| 4,200,746 | 4/1980 | Cook et al. | 544/25 |
| 4,278,793 | 7/1981 | Dürckheimer et al. | 544/27 |
| 4,315,005 | 2/1982 | Aymes et al. | 544/25 |
| 4,336,253 | 6/1982 | Lunn et al. | 544/25 |
| 4,394,384 | 7/1983 | Takaya et al. | 544/25 |
| 4,399,131 | 8/1983 | Dürckheimer et al. | 544/25 |
| 4,430,499 | 2/1984 | Wheeler | 544/25 |
| 4,470,983 | 9/1984 | Blumbach et al. | 544/21 |
| 4,477,659 | 10/1984 | Nishikido et al. | 544/27 |

Primary Examiner—Nicholas S. Rizzo
Attorney, Agent, or Firm—Finnegan, Henderson, Farabow, Garrett & Dunner

[57] ABSTRACT

Novel cephalosporin compounds having antibacterial activity, which are represented by the following compounds of the general formula (I),

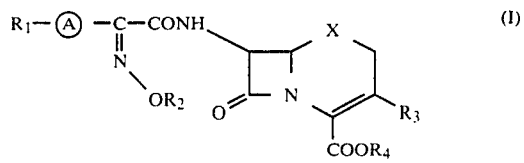

wherein
$R_1$ represents an amino group or a protected amino group;
Ⓐ represents a 5- or 6-membered heterocyclic ring containing therein 1 to 4 nitrogen, oxygen or sulfur atoms;
$R_2$ represents a normal alkyl group having 1 to 6 carbon atoms, a branched alkyl group having 3 to 6 carbon atoms, an alkoxyalkyl group having 2 to 6 carbon atoms, a cycloalkyl group having 3 to 6 carbon atoms; a cycloalkenyl group having 3 to 6 carbon atoms; an aromatic organic residue; a 3- to 6-membered heterocyclic ring containing 1 to 4 nitrogen, sulfur or oxygen atoms or,

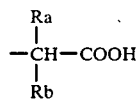

wherein Ra and Rb each, which may be the same or different, represents a hydrogen atom or an alkyl group having 1 to 4 carbon atoms;
$R_3$ represents an organic residue containing an amino group or a protected amino group and a carboxyl group or a protected carboxyl group;
X represents a sulfur atom or an oxygen atom; and
$R_4$ represents a hydrogen atom or a protective group of carboxyl group.

The general formula (I) described above can also be used as physiologically acceptable addition salts.

The compounds exhibit excellent intestinal absorption as well as high blood concentration and longer biological half-life.

8 Claims, 1 Drawing Figure

CEPHALOSPORIN COMPOUNDS

DESCRIPTION

1. Technical Field

The present invention relates to novel cephalosporin derivatives and more particularly to cephalosporin derivatives having antibacterial activity.

2. Background Art

Cephalosporin compounds have been widely used for treatment and prophylaxis of infectious diseases caused by pathogenic bacteria. It is often desirable to use cephalosporin antibiotics showing activities against both gram-positive bacteria and gram-negative bacteria and various types of cephalosporins having a wide range spectrum have been actively developed.

However, a cephalosporin compound showing high blood concentration and longer biological half-life, and further having an improved intestinal absorption has not been available heretofore.

Thus the present invention has been accomplished to improve the above-described drawbacks.

DISCLOSURE

Figure 1:
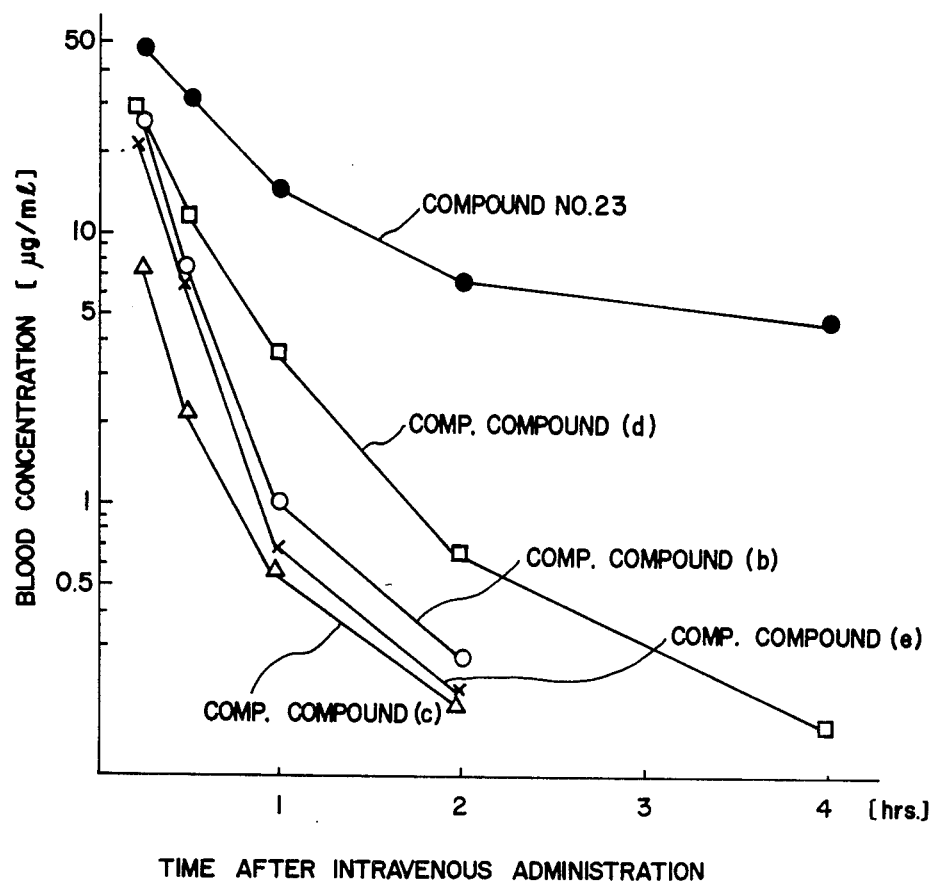
FIG. 1 shows blood concentration of Compound No. 23, Comparative Compounds (b), (c), (d) and (e) after intravenous administration in rat.

The present invention relates to novel cephalosporin derivatives having antibacterial activity, which are represented by the following general formula (I), $$R_1-\text{(A)}-\underset{\underset{\underset{OR_2}{N}}{\overset{\|}{N}}}{\overset{}{C}}-CONH\begin{array}{c}\text{[β-lactam-cephem structure]}\end{array} \quad (I)$$

wherein

R$_1$ represents an amino group or a protected amino group;

(A) represents a 5- or 6-membered heterocyclic ring containing therein 1 to 4 nitrogen, oxygen or sulfur atoms;

R$_2$ represents a normal alkyl group having 1 to 6 carbon atoms, a branched alkyl group having 3 to 6 carbon atoms, an alkoxyalkyl group having 2 to 6 carbon atoms, a cycloalkyl group having 3 to 6 carbon atoms; a cycloalkenyl group having 3 to 6 carbon atoms; an aromatic organic residue; a 3- to 6-membered heterocyclic ring containing 1 to 4 nitrogen, sulfur or oxygen atoms or, $$-\underset{\underset{R_b}{|}}{\overset{\overset{R_a}{|}}{C}}H-COOH$$

wherein Ra and Rb each, which may be the same or different, represents a hydrogen atom or an alkyl group having 1 to 4 carbon atoms;

R$_3$ represents an organic residue containing an amino group or a protected amino group and a carboxyl group or a protected carboxyl group;

X represents a sulfur atom or an oxygen atom; and

R$_4$ represents a hydrogen atom or a protective group of carboxyl group.

The general formula (I) described above can also be physiologically acceptable addition salts.

The cephalosporins according to the present invention are cephalosporins containing an organic residue containing an amino group or a protected amino group and a carboxyl group or a protected carboxyl group, as a substituent at the 3-position thereof. In the case of employing α-amino acids, optical isomers are present and any of the isomers can be used.

R$_3$ according to the present invention represents an organic residue containing an amino group or a protected amino group and a carboxyl group or a protected carboxyl group. Further, an organic residue according to the present invention includes an aromatic group such as phenyl and benzyl groups, an alkyl group containing 1 to 6 carbon atoms, a cycloalkyl group such as cyclopentyl and cyclohexyl groups or a heterocyclic group such as imidazole, thiadiazole.

A protective group of carboxyl group according to the present invention includes a lower alkyl group such as methyl, ethyl and propyl, benzyl, p-nitrobenzyl, tert-butyl, methoxy methyl, acetoxy methyl, pivaloyloxy methyl and trimethylsilyl groups.

A protective group of amino group according to the present invention includes formyl, acetyl, tert-butyloxycarbonyl, benzyloxycarbonyl, p-toluenesulfonyl, chloroacetyl and trimethylsilyl groups.

As the substituents at the substituents containing an amino group or a protected amino group and a carboxyl group or a protected carboxyl group attached directly to the heterocyclic ring of the 5- or 6-membered ring containing therein 1 to 4 nitrogen, sulfur or oxygen atoms, or at the side chain thereof are preferably employed. Specific examples of such substituents include groups described below:

$$-CH_2S-\underset{\underset{R_7}{|}}{\overset{}{\underset{N}{\bigg\langle}}}\overset{N}{\underset{}{\bigg\rangle}}-CH_2-\underset{\underset{R_6}{|}}{\overset{}{C}}H-COOR_5,$$

$$-CH_2S-\underset{S}{\overset{N-\!\!\!-\!\!\!-N}{\bigg\langle\!\!\bigg\rangle}}-CH_2-\underset{\underset{R_6}{|}}{\overset{}{C}}H-COOR_5,$$

$$-CH_2S-\underset{O}{\overset{N-\!\!\!-\!\!\!-N}{\bigg\langle\!\!\bigg\rangle}}-CH_2-\underset{\underset{R_6}{|}}{\overset{}{C}}H-COOR_5,$$

$$-CH_2S-\underset{\underset{R_7}{|}}{\overset{}{\underset{N}{\bigg\langle}}}\overset{N}{\underset{}{\bigg\rangle}}\begin{array}{c}COOR_5\\NH-R_6\end{array},$$

-continued

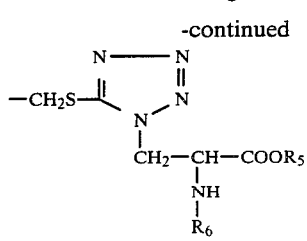

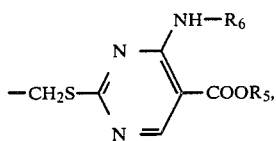

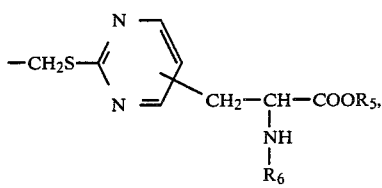

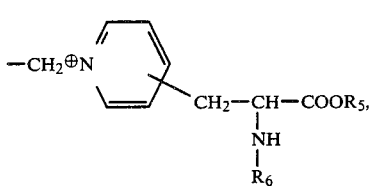

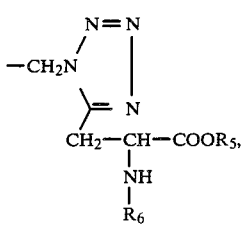

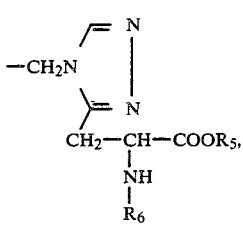

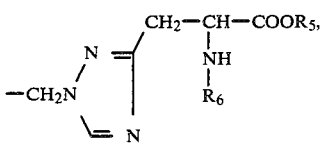

and

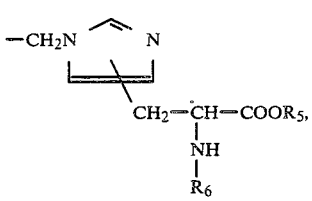

wherein $R_5$ represents a hydrogen atom or a protective group of a carboxyl group; $R_6$ represents a hydrogen atom or a protective group of an amino group; and $R_7$ represents a hydrogen atom, a normal alkyl group 1 to 6 carbon atoms or a branched alkyl group having 3 to 6 carbon atoms.

Of these, the following groups are particularly preferred in view of high antibacterial activity and improved intestinal absorption:

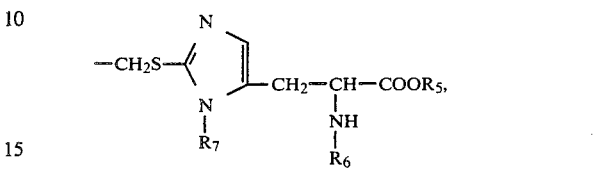

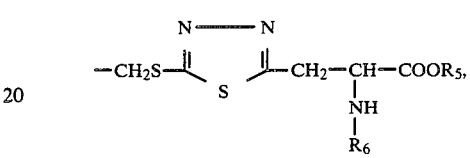

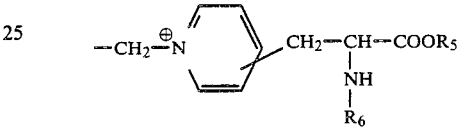

and

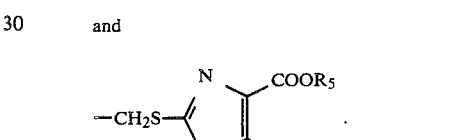

As the Ⓐ moiety in the 7-position substituent,

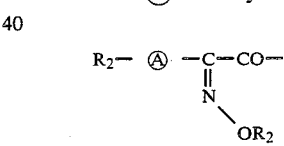

the following groups can be listed:

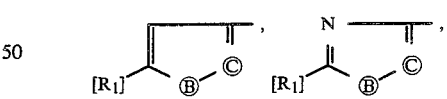

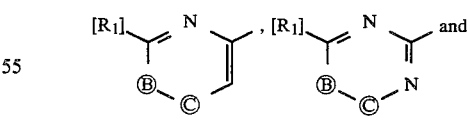

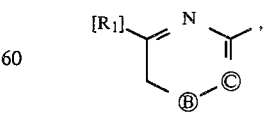

wherein Ⓑ represents any one of —S—, —NH—, —N= and —O—; Ⓒ represents —CH—, —NH— or —N=; and $R_1$ is an amino group or a protective group of amino group.

Of these, preferred 7-position substituents are

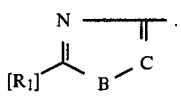

Specific examples of preferred substituents at the 7-position include:

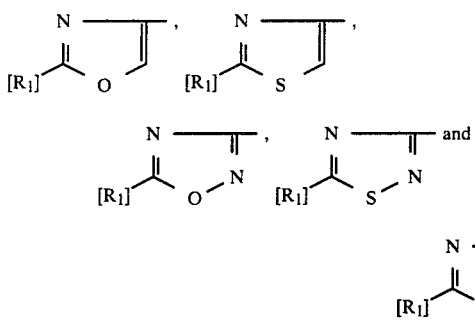

In the foregoing 7-position substituents, the oximino group takes syn-configuration and anti-configuration, and syn-configuration is preferable.

$R_1$ represents an amino group or a protected amino group. The protective group of amino group is exemplified by formyl, acetyl, tert-butyloxycarbonyl, benzyloxycarbonyl, p-toluenesulfonyl, chloroacetyl, trimethylsilyl groups, etc.; and further other groups which can be combined with an amino group and is chemically or physiologically eliminable, may be used as the protective group.

$R_2$ represents, as has been described above, a normal alkyl group having 1 to 6 carbon atoms, a branched alkyl group having 3 to 6 carbon atoms, an alkoxyalkyl group having 2 to 6 carbon atoms, a cycloalkyl group having 3 to 6 carbon atoms, a cycloalkenyl group having 3 to 6 carbon atoms, an aromatic organic residue, a 3- to 6-membered heterocyclic ring containing therein 1 to 4 nitrogen, sulfur or oxygen atoms, or,

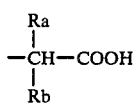

wherein Ra and Rb each, which may be the same or different, represents a hydrogen atom or an alkyl group having 1 to 4 carbon atoms.

Examples of a normal alkyl group having 1 to 6 carbon atoms include methyl, ethyl, propyl, butyl, pentyl, hexyl. Examples of a branched alkyl group having 3 to 6 carbon atoms include isopropyl, isobutyl, isopentyl, isohexyl.

Representative examples of alkoxyalkyl groups having 2 to 6 carbon atoms include:

—CH$_2$OCH$_3$,

—CH$_2$OCH$_2$CH$_3$,

—CH$_2$OCH$_2$CH$_2$CH$_3$,

—CH$_2$CH$_2$OCH$_3$,

—CH$_2$CH$_2$OCH$_2$CH$_3$,

—CH$_2$CH$_2$OCH$_2$CH$_2$CH$_3$, and

—CH$_2$CH$_2$OCH$_2$CH$_2$CH$_2$CH$_3$.

Examples of cycloalkyl groups having 3 to 6 carbons include:

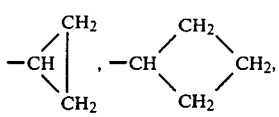

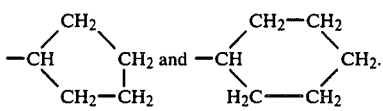

Specific examples of cycloalkenyl groups having 3 to 6 carbon atoms include:

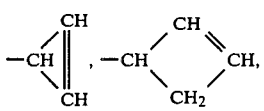

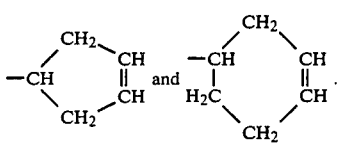

Exemplary aromatic organic residues include a phenyl group, a benzyl group, and these groups containing therein substituents such as —NO$_2$, —Cl, —Br, —I, —F, —CN, —CH$_3$ and —OCH$_3$.

Further exemplary 3- to 6-membered heterocyclic ring containing therein 1 to 4 nitrogen, sulfur or oxygen atoms include:

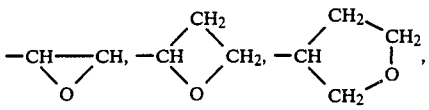

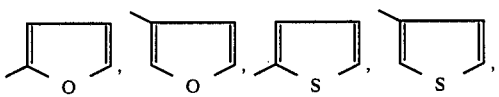

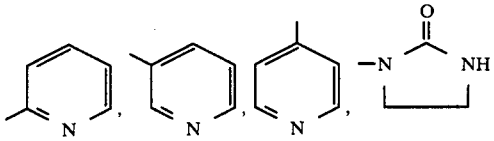

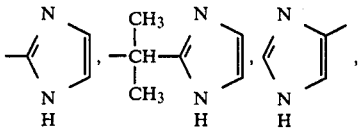

-continued

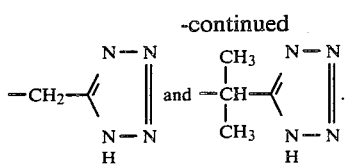

Ra and Rb each of

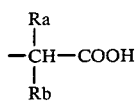

may be the same or different group, and is exemplified by hydrogen, methyl, ethyl, propyl and butyl group.

In this connection, as the (A) moiety at the 7-position,

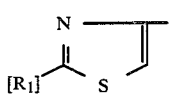

is particularly preferably employed. In this case, preferred examples of $R_2$ at the 7-position include normal alkyl groups having 1 to 6 carbon atoms, for example, a methyl, ethyl, propyl, butyl, pentyl or hexyl group; branched alkyl groups having 3 to 6 carbon atoms, for example, an isopropyl, isobutyl, isopentyl, isohexyl group, or the like; and further,

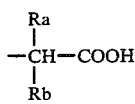

wherein Ra and Rb each represents, which may be the same or different, a hydrogen atom or alkyl groups having 1 to 4 carbon atoms, for example, a methyl, ethyl, propyl or butyl group.

$R_4$ and $R_5$ described as above represent a hydrogen atom or a protective group of a carboxyl group; as the protective group of a carboxyl group, lower alkyl groups such as methyl, ethyl, propyl, etc.; a benzyl group; a p-nitrobenzyl group; a tert-butyl group; a methoxymethyl group; an acetoxymethyl group; a pivaloyloxymethyl group; a trimethylsilyl group; etc. are employed.

$R_6$ described above represents a hydrogen atom or a protective group of an amino group; exemplary protective groups of an amino group include a formyl group, an acetyl group, a tert-butyloxycarbonyl group, a benzyloxycarbonyl group, a p-toluenesulfonyl group, a chloroacetyl group, a trimethylsilyl group, etc.

$R_7$ represents a hydrogen atom, a normal alkyl group having 1 to 6 carbon atoms or a branched alkyl group having 3 to 6 carbon atoms. Exemplary alkyl groups having 1 to 6 carbon atoms include a methyl, ethyl, propyl, butyl, pentyl or hexyl group; exemplary branched alkyl groups having 3 to 6 carbon atoms include an isopropyl, isobutyl, isopentyl or isohexyl group, etc.

In the general formulae (XI) and (XII) described later, (D) represents a leaving group such as —O $COR_8$ ($R_8$ represents an alkyl group having 1 to 6 carbon atoms) or a halogen atom exemplified by chlorine, bromine, iodine or fluorine atom. Examples of an alkyl group having 1 to 6 carbon atoms are exemplified by methyl, ethyl, propyl, butyl, pentyl, hexyl, isopropyl, isobutyl, isopentyl and isohexyl groups.

Furthermore, the cephalosporin compound according to the present invention can be used as a physiologically acceptable addition salt thereof. Suitable examples of such addition salts as above include salts of the cephalosporin compound of the present invention with inorganic acids such as hydrochloric acid, hydrobromic acid, hydroiodic acid, sulfuric acid, phosphoric acid and nitrile acid; salts of the compound with organic acids such as formic acid, acetic acid, propionic acid, succinic acid, lactic acid, maleic acid, fumaric acid, malonic acid, oxalic acid, citric acid, tartric acid, malic acid, mucic acid, gluconic acid, benzoic acid, salicyclic acid, 1,5-naphthalenedisulfonic acid, ascorbic acid, phenylacetic acid, p-aminosalicyclic acid, methanesulfonic acid, ethanesulfonic acid, hydroxyethanesulfonic acid, benzenesulfonic acid, p-toluenesulfonic acid, glutamic acid and aspartic acid; saccharates of the compound; alkaline salts of the compound such as sodium salt and potassium salt; and salts of the compound with basic organic compounds such as lysine, histidine and alginine.

Specific examples of the compounds according to the present invention are shown below:

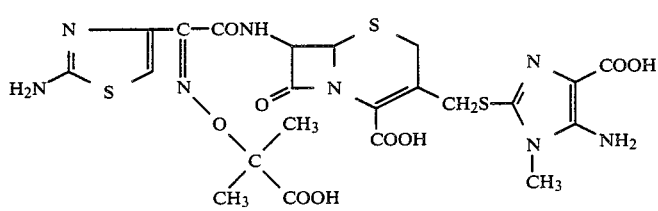

Compound No. 1

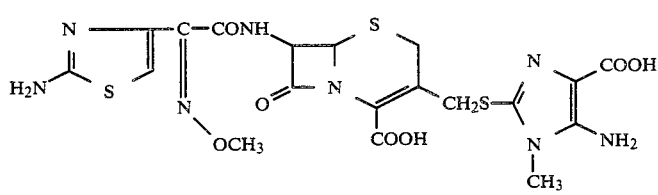

Compound No. 2

-continued
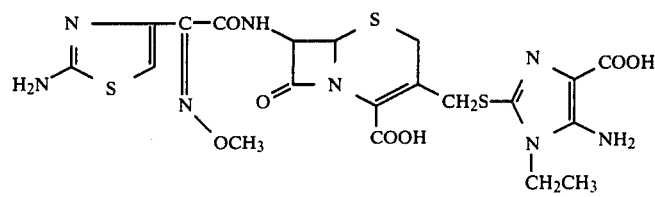
Compound No. 3
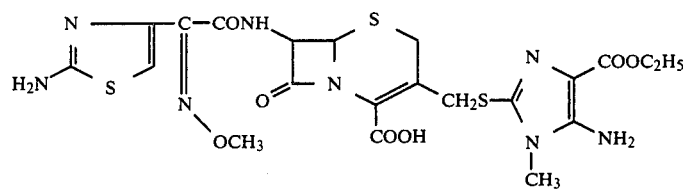
Compound No. 4
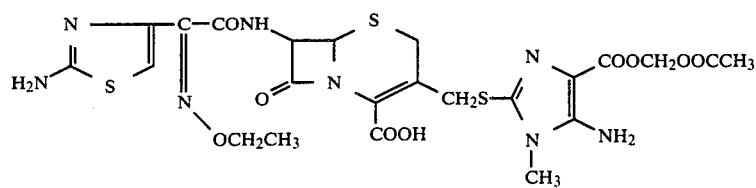
Compound No. 5
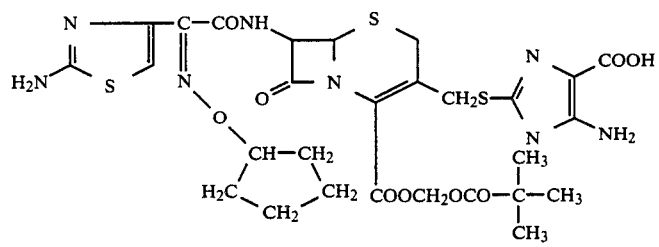
Compound No. 6
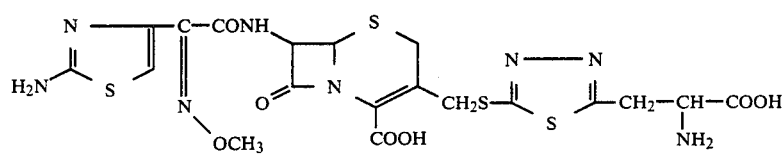
Compound No. 7
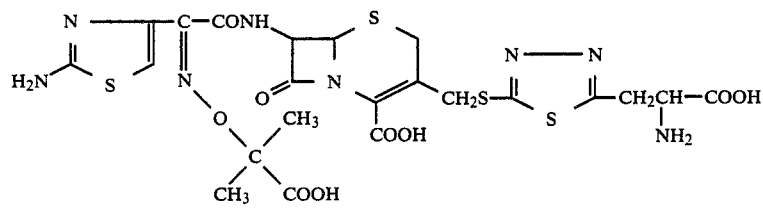
Compound No. 8
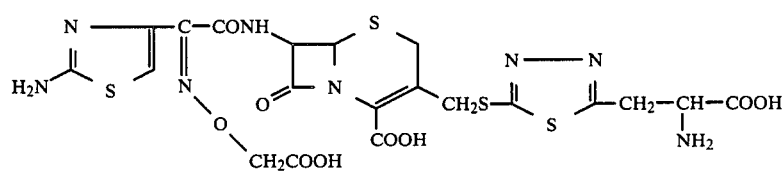
Compound No. 9
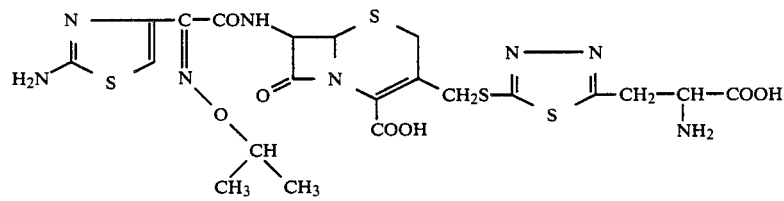
Compound No. 10

-continued
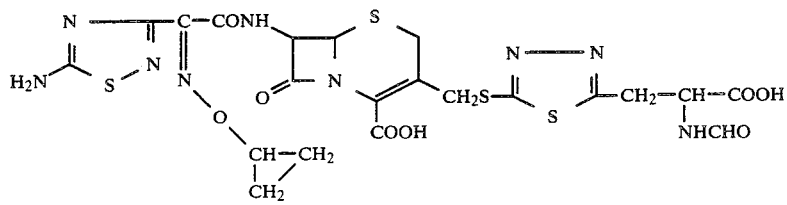
Compound No. 11
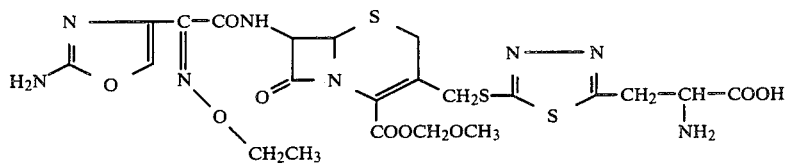
Compound No. 12
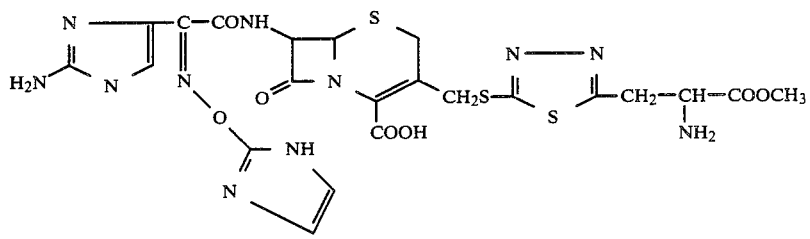
Compound No. 13
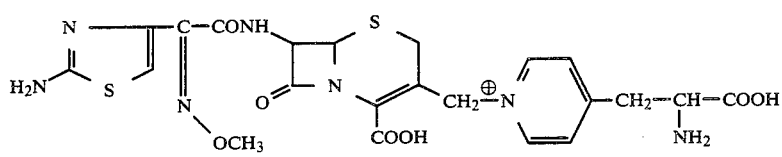
Compound No. 14
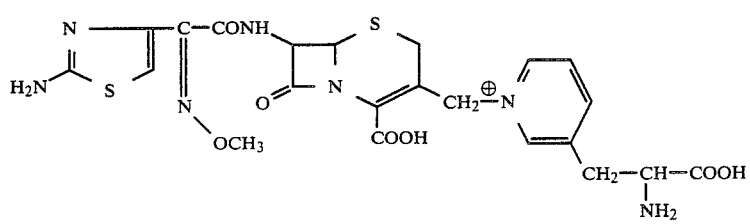
Compound No. 15
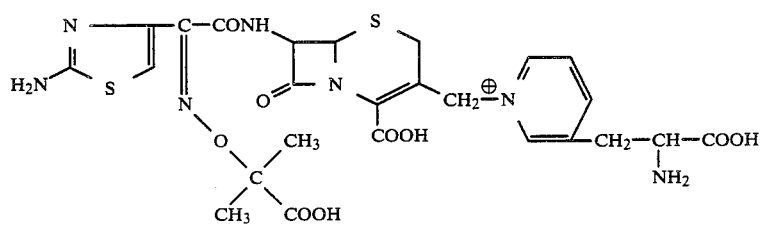
Compound No. 16
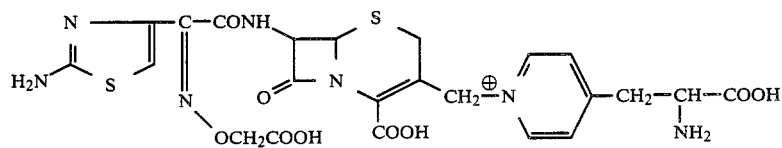
Compound No. 17
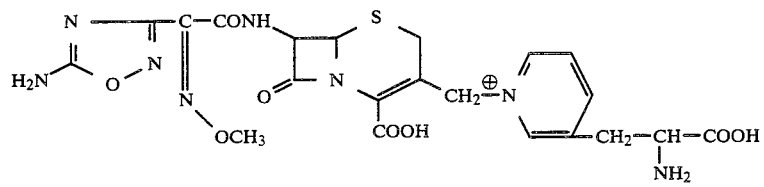
Compound No. 18

-continued
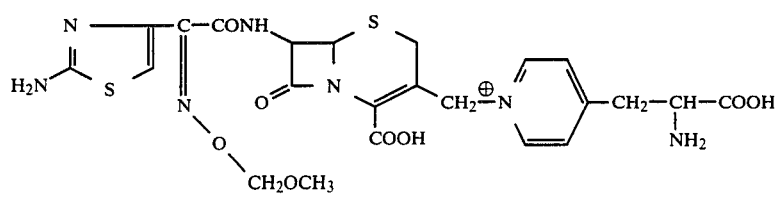
Compound No. 19
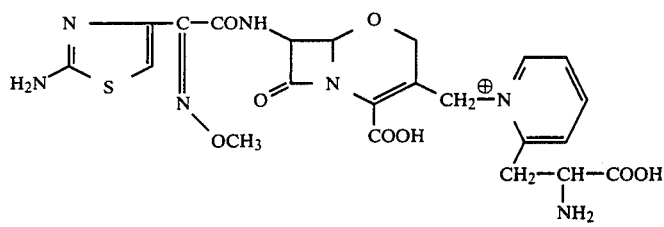
Compound No. 20
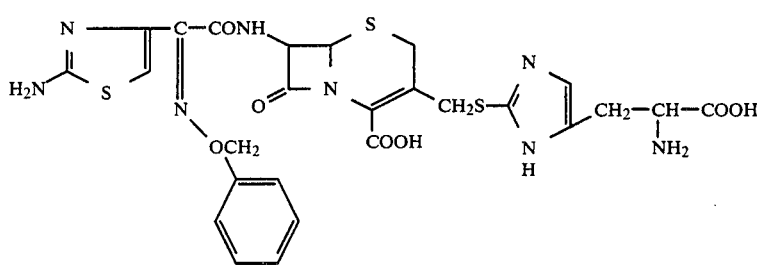
Compound No. 21
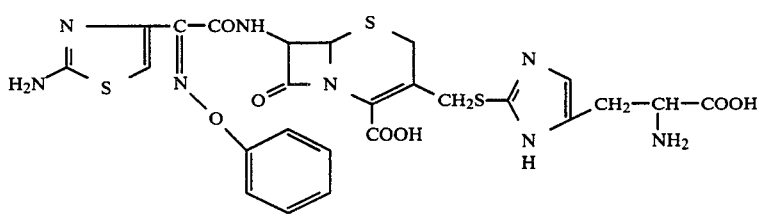
Compound No. 22
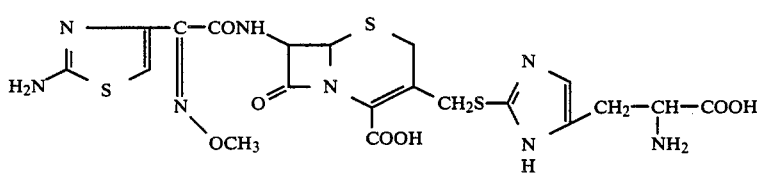
Compound No. 23
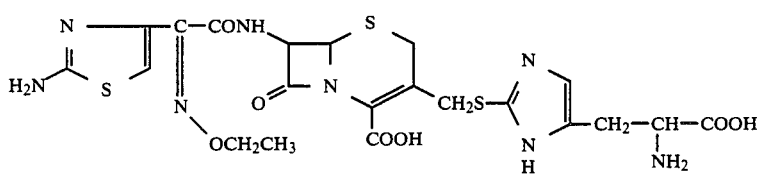
Compound No. 24
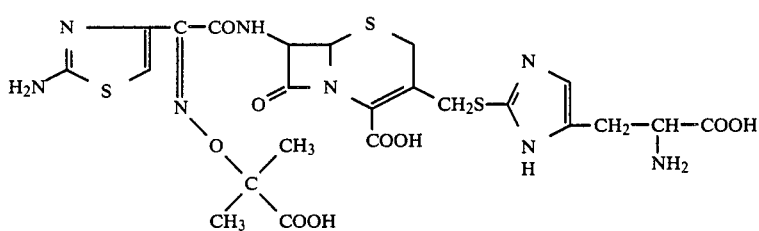
Compound No. 25

-continued
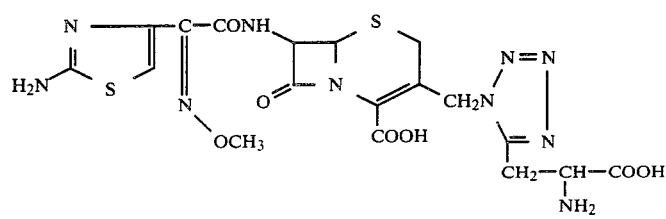
Compound No. 26
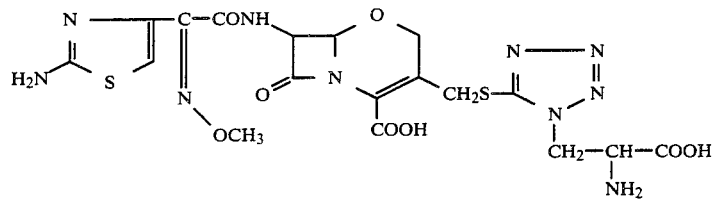
Compound No. 27
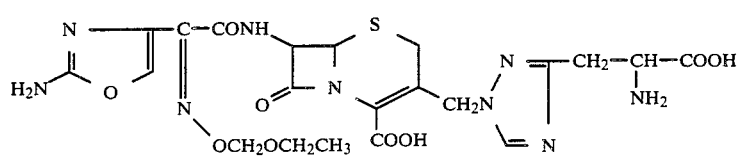
Compound No. 28
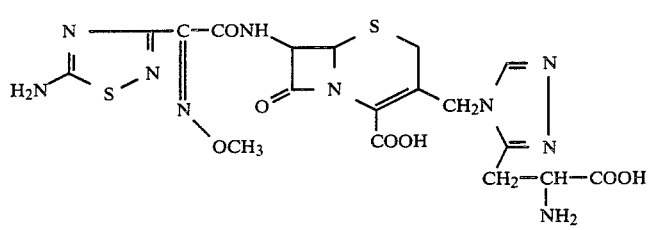
Compound No. 29
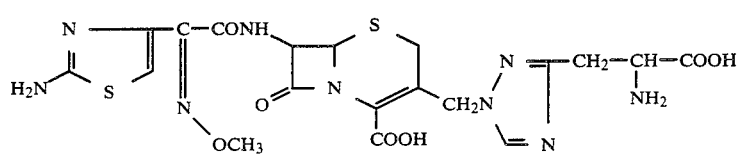
Compound No. 30
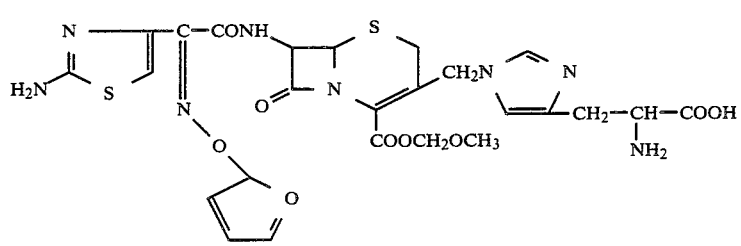
Compound No. 31
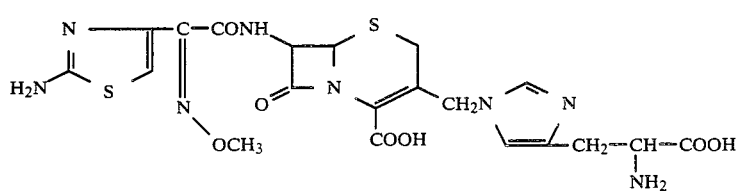
Compound No. 32
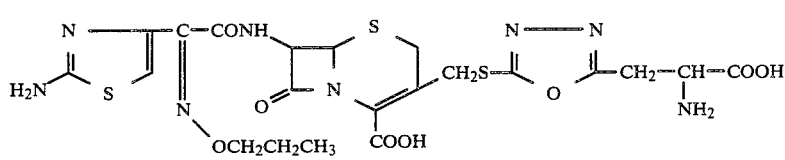
Compound No. 33

-continued
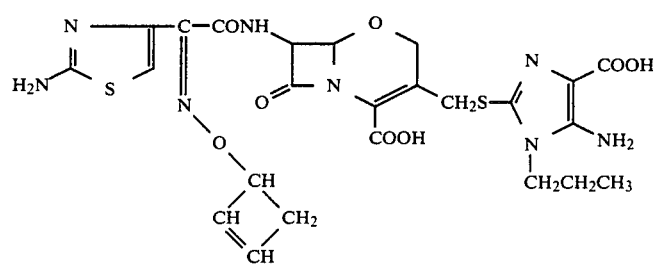
Compound No. 34
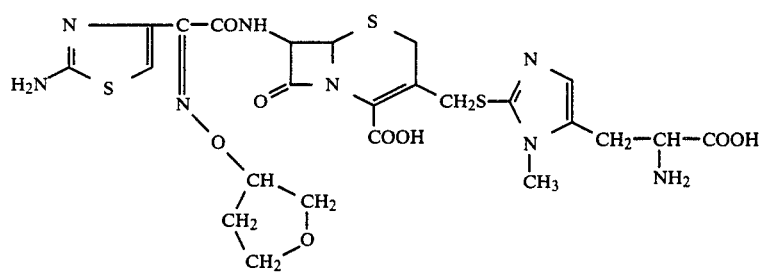
Compound No. 35
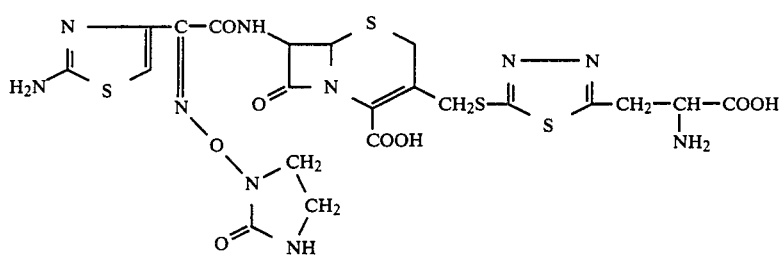
Compound No. 36
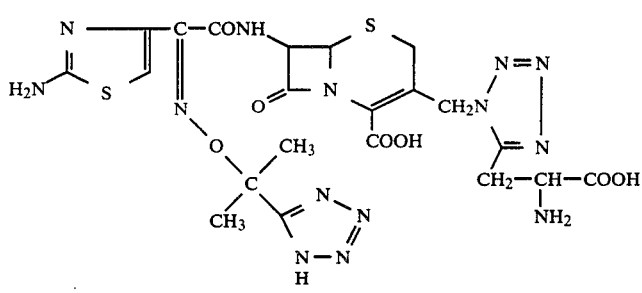
Compound No. 37
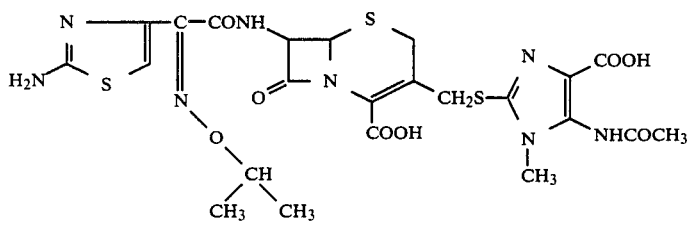
Compound No. 38
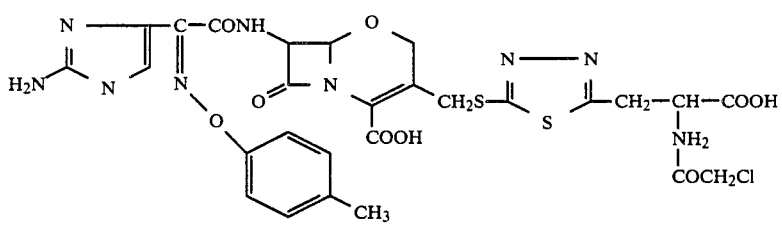
Compound No. 39

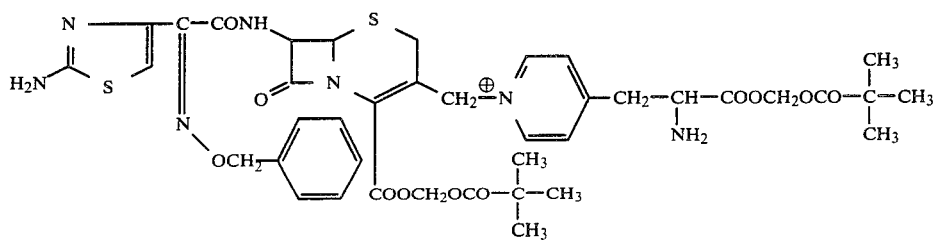

Compound No. 40

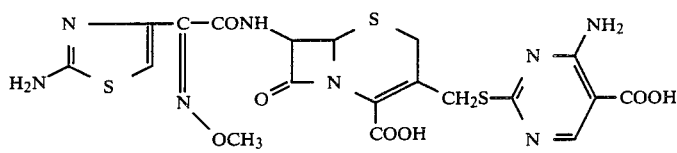

Compound No. 41

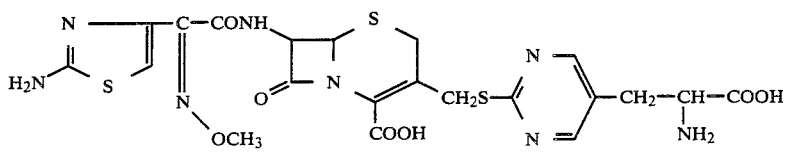

Compound No. 42

Nextly, antibacterial activity or minimum inhibitory concentration (MIC) was measured and the results are shown in Table 1 with respect to the following representative compounds according to the present invention.

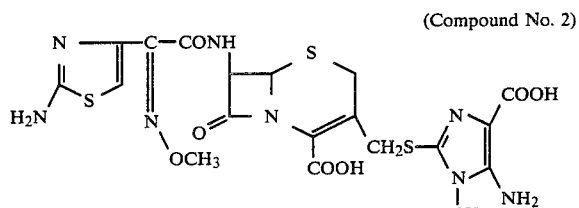

(Compound No. 2)

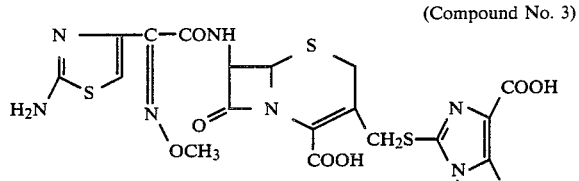

(Compound No. 3)

TABLE 1

| Minimum Inhibitory Concentration (MIC) | | | |
|---|---|---|---|
| | Bacterial Count Inoculated: $10^6$ cells/ml | | |
| | Compound No. 2 | Compound No. 3 | Comparative Compound (a) |
| Staph. aureus ATCC 6538P | 3.1 | 1.6 | 0.4 |

TABLE 1-continued

| Minimum Inhibitory Concentration (MIC) | | | |
|---|---|---|---|
| | Bacterial Count Inoculated: $10^6$ cells/ml | | |
| | Compound No. 2 | Compound No. 3 | Comparative Compound (a) |
| Staph. aureus MS27 | 6.3 | 1.6 | 1.6 |
| Strept. pyogenes NY5 | 0.1 | ≦0.1 | 0.2 |
| Sarcina lutea ATCC 9341 | 0.2 | ≦0.1 | 0.8 |
| E. coli NIHJ-JC2 | 0.2 | ≦0.1 | 1.6 |
| E. coli W3630 | 0.2 | 0.2 | 3.1 |
| E. coli W3630 PS3 | 0.2 | ≦0.1 | 3.1 |
| Citrobact. freundii GN346 | 25 | 25 | >100 |
| Klebs. pneumoniae ATCC 10031 | 0.1 | ≦0.1 | 3.1 |
| Salm. enteritidis Gaertner | 0.2 | 0.2 | 3.1 |
| Shigella sonnei E33 | 0.4 | 0.2 | 1.6 |
| Proteus morganii 0239 | 0.1 | ≦0.1 | >100 |
| Proteus rettgeri ACR | 0.2 | ≦0.1 | >100 |
| Enterobact. aerogenes 0655 | 1.6 | 1.6 | >100 |
| Enterobact. cloacae GN336 | 0.8 | 0.2 | >100 |
| Serratia marcescens | 0.2 | 0.8 | >100 |
| Ps. aerugisiosa 0812 M2 | 6.3 | 3.1 | >100 |

Footnote of Table 1
Comparative Compound (a):

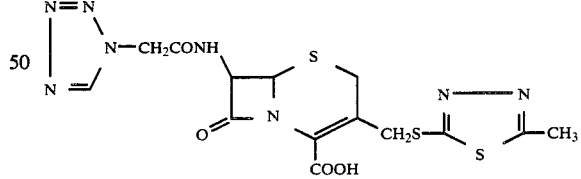

With respect to Compound Nos. 14 and 15, antibacterial activity or minimum inhibitory concentration (MIC) was measured and the results are shown in Table 2.

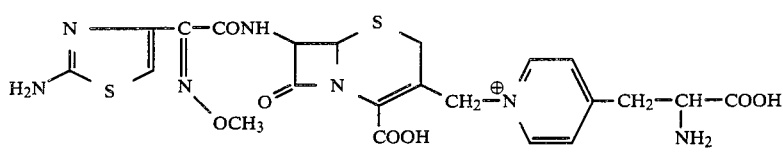

(Compound No. 14)

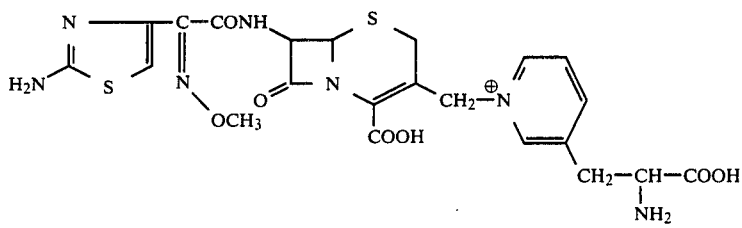

(Compound No. 15)

TABLE 2

Minimum Inhibitory Concentration (MIC)

Bacterial Count Inoculated: $10^6$ cells/ml

| | Compound No. 14 | Compound No. 15 | Comparative Compound (a) |
|---|---|---|---|
| Staph. aureus ATCC 6538P | 6.3 | 3.1 | 0.4 |
| Staph. aureus MS27 | 3.1 | 6.3 | 1.6 |
| Strept. pyogenes NY5 | 0.1 | ≦0.1 | 0.2 |
| Sarcina lutea ATCC 9341 | 0.8 | ≦0.1 | 0.8 |
| Bac. subtilis ATCC 6633 | ≦0.1 | 1.6 | 0.2 |
| E. coli NIHJ-JC2 | 0.1 | 0.2 | 1.6 |
| E. coli W3630 | ≦0.1 | 0.2 | 3.1 |
| E. coli W3630 PS3 | ≦0.1 | 0.1 | 3.1 |
| Citrobact. freundii GN346 | 12.5 | 12.5 | >100 |
| Klebs. pneumoniae ATCC 10031 | ≦0.1 | 0.1 | 3.1 |
| Salm. enteritidis Gaertner | ≦0.1 | ≦0.1 | 3.1 |
| Shigella sonnei E33 | ≦0.1 | ≦0.1 | 1.6 |
| Proteus morganii 0239 | 0.2 | 0.2 | >100 |
| Proteus rettgeri ACR | 0.2 | 0.2 | >100 |
| Enterobact. aerogenes 0655 | 0.2 | 0.2 | >100 |
| Enterobact. cloacae GN336 | 0.2 | 0.2 | >100 |
| Serratia marcescens | 0.1 | 0.4 | >100 |
| Ps. aeruginosa 0812 M2 | 3.1 | 6.3 | >100 |

Footnote of Table 2
Comparative Compound (a):

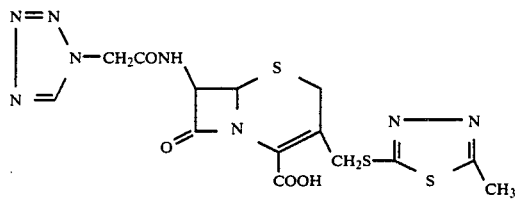

The minimum inhibitory concentration (MIC) of Compound No. 23 was measured and the results are shown in Table 3.

TABLE 3

Minimum Inhibitory Concentration (MIC)

Bacterial Count Inoculated: $10^6$ cells/ml

| | Compound No. 23 | Comparative Compound (b) |
|---|---|---|
| E. coli NIHJ-JC2 | ≦0.2 | 0.8 |
| E. coli W3630 | ≦0.2 | ≦0.2 |
| E. coli W3630 RGN14 | ≦0.2 | ≦0.2 |
| E. coli W3630 RGN238 | ≦0.2 | ≦0.2 |
| E. coli 0205 | 0.4 | 0.4 |
| Klebs. pneumoniae ATCC10031 | ≦0.2 | ≦0.2 |
| Shigella sonnei E33 | ≦0.2 | ≦0.2 |
| Proteus rettgeri ACR | ≦0.2 | ≦0.2 |
| Enterobact. cloacae GN336 | ≦0.2 | ≦0.2 |
| Serratia marcescens | ≦0.2 | ≦0.2 |
| E. coli NIHJ-JC2 | 12.5 | 25 |
| E. coli W3630 | 6.3 | 6.3 |
| E. coli W3630 RGN14 | 6.3 | 100 |
| E. coli W3630 RGN238 | 25 | ≧100 |
| E. coli 0205 | 12.5 | 50 |
| Klebs. pneumoniae ATCC10031 | 1.6 | 1.6 |
| Shigella sonnei E33 | 1.6 | 3.1 |
| Proteus rettgeri ACR | 25 | 100 |
| Enterobact. cloacae GN336 | 25 | 50 |
| Serratia marcescens | >100 | >100 |

Footnote of Table 3
Comparative Compound (b):

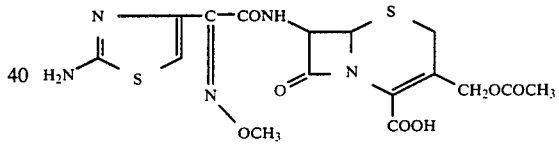

The minimum inhibitory concentration (MIC) of Compound No. 7 was measured and the results are shown in Table 4.

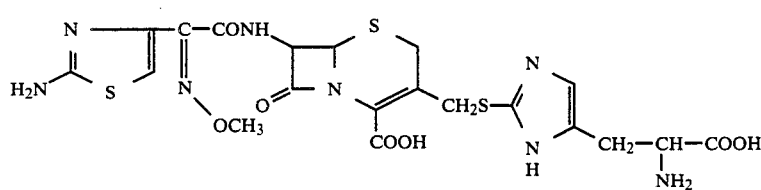

(Compound No. 23)

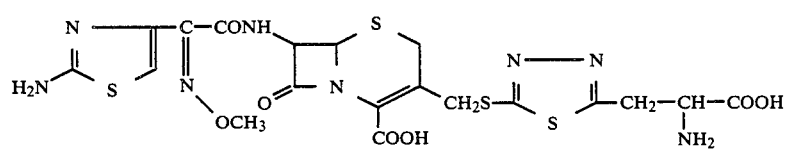

(Compound No. 7)

TABLE 4

Minimum Inhibitory Concentration (MIC)

| | Compound No. 7 | Comparative Compound (b) | Comparative Compound (c) |
|---|---|---|---|
| Bacterial Count Inoculated: $10^6$ cells/ml | | | |
| Staph. aureus ATCC 6538P | 1.6 | 1.6 | 1.6 |
| Staph. aureus MS27 | 3.1 | 1.6 | 3.1 |
| Staph. pyogenes NY5 | ≦0.2 | ≦0.2 | ≦0.2 |
| Sarcina lutea ATCC9341 | ≦0.2 | ≦0.2 | ≦0.2 |
| E. coli NIHJ-JC2 | 0.4 | ≦0.2 | ≦0.2 |
| E. coli W3630 | ≦0.2 | ≦0.2 | 0.4 |
| E. coli W3630 PS3 | ≦0.2 | ≦0.2 | ≦0.2 |
| Citrobact. freundii GN346 | 50 | 25 | 50 |
| Klebs. pneumoniae ATCC10031 | ≦0.2 | ≦0.2 | ≦0.2 |
| Salm. enteritidis Gaertner | ≦0.2 | ≦0.2 | 0.4 |
| Shigella sonnei E33 | ≦0.2 | ≦0.2 | ≦0.2 |
| Proteus morganii 0239 | ≦0.2 | ≦0.2 | 0.8 |
| Enterobact. aerogenes 0655 | ≦0.2 | ≦0.2 | 0.8 |
| Enterobact. cloacae GN336 | ≦0.2 | ≦0.2 | ≦0.2 |
| Serratia marcescens | ≦0.2 | ≦0.2 | 0.8 |
| Bacterial Count Inoculated: $10^8$ cells/ml | | | |
| Staph. aureus ATCC 6538P | 3.1 | 3.1 | 1.6 |
| Staph. aureus MS27 | 3.1 | 3.1 | 50 |
| Staph. pyogenes NY5 | 0.2 | 0.2 | 0.4 |
| Sarcina lutea ATCC9341 | ≦0.2 | ≦0.2 | ≦0.2 |
| E. coli NIHJ-JC2 | 0.2 | 6.3 | 6.3 |
| E. coli W3630 | 0.8 | 25 | 25 |
| E. coli W3630 PS3 | 1.6 | 25 | 25 |
| Citrobact. freundii GN346 | 100 | 100 | >100 |
| Klebs. pneumoniae ATCC10031 | 0.8 | 25 | >100 |
| Salm. enteritidis Gaertner | 3.1 | 6.3 | 50 |
| Shigella sonnei E33 | 0.2 | 1.6 | ≦0.2 |
| Proteus morganii 0239 | 25 | 50 | >100 |
| Enterobact. aerogenes 0655 | 25 | 50 | >100 |
| Enterobact. cloacae GN336 | 12.5 | 50 | 50 |
| Serratia marcescens | 100 | 50 | >100 |

Footnote of Table 4
Comparative Compound (b):

[Chemical structure of Comparative Compound (b)]

Comparative Compound (c):

[Chemical structure of Comparative Compound (c)]

In addition to excellent antibacterial activity, the compounds of the present invention are low in toxicity. For example, in acute toxicity test using mice, the following results were obtained with Compound Nos. 2, 3, 7, 14, 15 and 23 which were intraperitoneally administered.

| Compound No. | $LD_{50}$ (g/kg) |
|---|---|
| 2 | 9–10 |
| 3 | 8–10 |
| 7 | 9–12 |
| 14 | 9–10 |
| 15 | 10–12 |
| 23 | 10–12 |

Further in the compounds according to the present invention, intestinal absorption is improved by the introduction of amino acids at the 3-position thereof. For example, comparison of the maximum blood concentration of the Compound Nos. 2, 3, 7, 8, 14, 15 and 23 with that of Comparative Compound (b) establishes and affirms the effects, as is shown below.

| | Maximum Blood Concentration ($\mu$g/ml) |
|---|---|
| (Comparative Compound (b)) | 0.2 |

-continued
| | Maximum Blood Concentration (μg/ml) |
|---|---|
| (Compound No. 2) 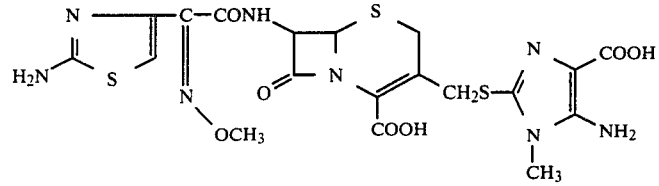 | 16 |
| (Compound No. 3) 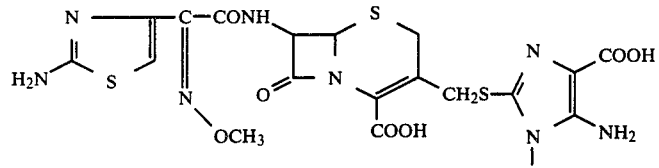 | 20 |
| (Compound No. 7) 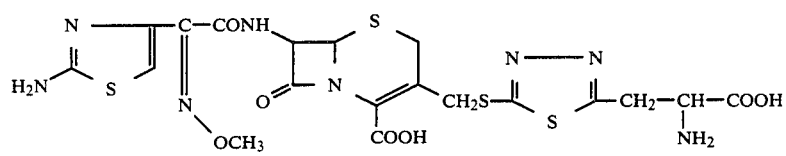 | 7 |
| (Compound No. 8) 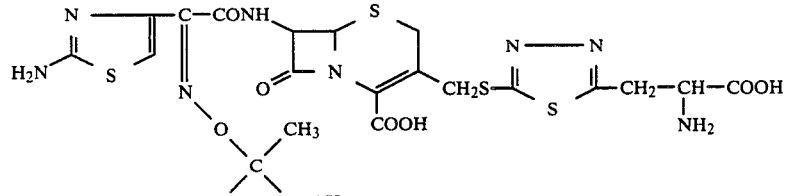 | 8 |
| (Compound No. 14) 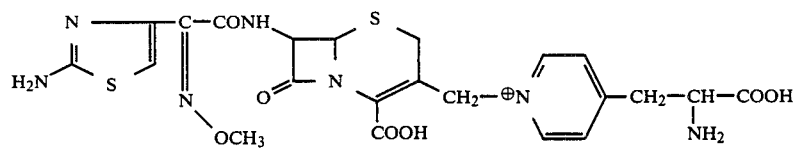 | 9 |
| (Compound No. 15) 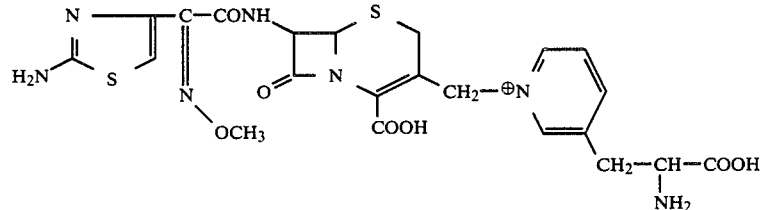 | 12 |
| (Compound No. 23) 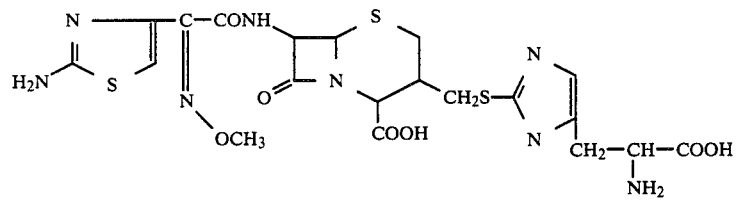 | 6 |

In the above test, the method for measurement of blood concentration was as follows.

Rate: Wister rat weighing 170 to 220 g
Dose: 30 mg/kg

Wister rats were fasted from the previous night but freely accessible to water.

Each of drugs was administered as a solution of pH 7 in a phosphate buffer, when orally administered.

The blood concentration was measured in accordance with the High Performance Liquid Chromatography (HPLC) method and the Bioassay method by using E. coli as bacteria for test.

The compounds of the present invention can be orally administered singly or with a pharmaceutically acceptable carrier or dilution agent. Exemplary carriers and dilution agents include lactose, saccharose, starch, cellulose, calcium sulfate, gelatin, etc. Such compositions can be administered in the form of a tablet or a capsule filled up therein. Further these compounds can also be administered as a suspension or a solution by mixing with a liquid.

One of the significant features of the compounds according to the present invention is to provide great effects on maintaining high blood concentration and longer biological half-life by introducing amino acids at the 3-position thereof. For example, a pattern of the blood concentration after intravenous injection of Compound No. 23 in rat is shown in FIG. 1. Compounds for comparison are Comparative Compounds (b), (c), (d) and (e) having the following chemical structures which are cephalosporins belonging to the third generation. It has been found and affirmed from the FIG. 1 that the compounds of the present invention have significant features of being extremely superior in high blood concentration and in longer biological half-life as compared with the comparative compounds.

Comparative Compound (b)

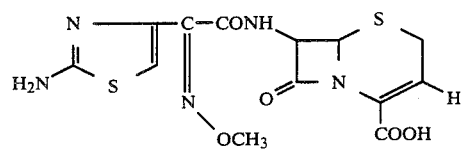

Comparative Compound (c)

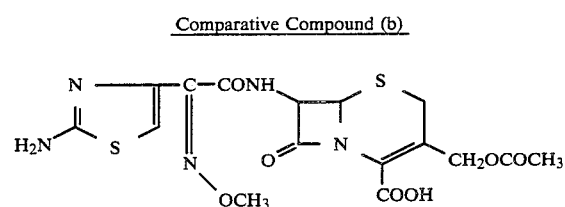

Comparative Compound (d)

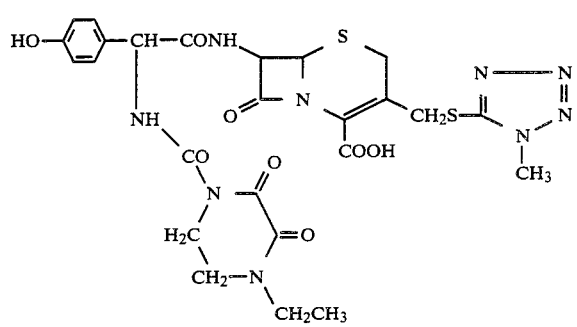

Comparative Compound (e)

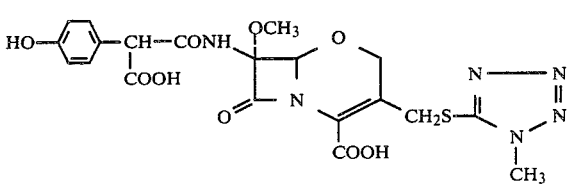

The cephalosporin compounds of the present invention represented by the general formula (I) can be prepared by the following two routes, when roughly classified.

(i) The first route is: a process for preparing a cephalosporin derivative represented by the general formula (I),

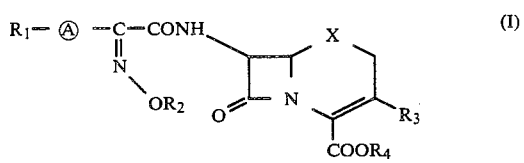

which comprises reacting a carboxylic acid derivative represented by the general formula (VIII), (VIII)

$R_1$—Ⓐ—C(=N-OR_2)—COOH or an active form of said carboxylic acid, with a 7-aminocephalosporanic acid derivative represented by the general formula (IX),

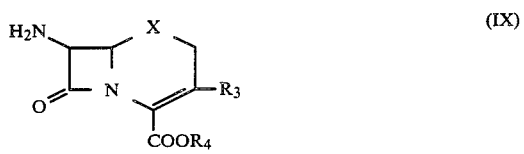

wherein $R_1$, $R_2$, $R_3$, $R_4$, X and A each represents the same meaning as defined before;

preferably, a process for preparing a cephalosporin derivative represented by the general formula (III),

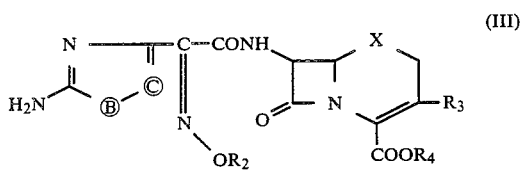

which comprises reacting a carboxylic acid derivative represented by the general formula (X),

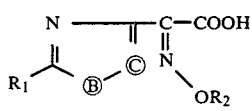 (X)

or an active form of said carboxylic acid, with a 7-aminocephalosporanic acid derivative represented by the general formula (IX),

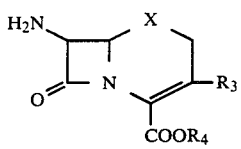 (IX)

and if necessary, removing a protective group of amino group, wherein $R_1$, $R_3$ and $R_4$ each represents the same meaning as defined before and $R_2$, Ⓑ and Ⓒ each the same meaning as defined before.

Further according to the reaction route (i), one example comprises protecting the amino group in 2-mercapto-5-(2-amino-2-carboxy)ethyl-1,3,4-thiadiazole, for example by t-butyloxycarbonylating the amino group, and then reacting with 7-aminocephalosporanic acid through the acetoxymethyl group at the 3-position thereof in a solvent mixture system of water and acetone using sodium hydrogencarbonate, etc. as a base, at 30° to 100° C. for 1 to 20 hours, while controlling pH in the range of 6 to 7. The resulting derivative was trimethylsilylated 7-aminocephalosporanic acid at the 4-position carboxyl group and/or at the carboxyl group of the 3-position 5-(2-amino-2-carboxy)ethyl-1,3,4-thiadiazole and/or at the 7-position amino group, and then is condensed with

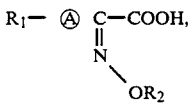

or with an activated form thereof such as an activated ester, a mixed acid anhydride or an acid chloride.

In this connection, exemplary activated esters include:

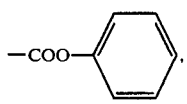

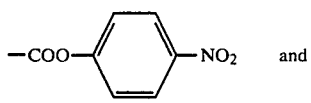 and

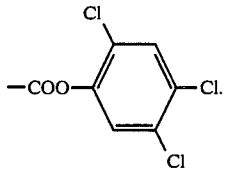

Exemplary mixed acid anhydrides include:

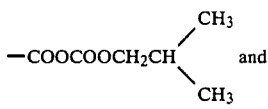 and

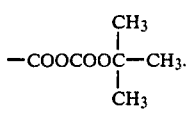

Exemplary acid chlorides include —COCl.

Then after the compound being de-tert-butylcarboxylated by trifluoroacetic acid or formic acid or other acid, the product purposed for can be obtained.

This route (i) can be shown by the following equation.

(i)

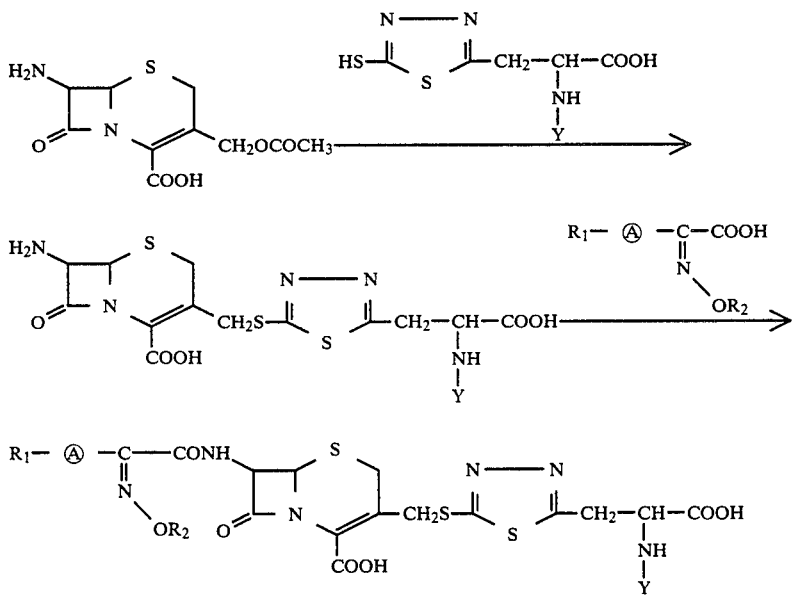

wherein Y is a protective group of amino group.

(ii) The second route is: a process for preparing a cephalosporin derivative which comprises reacting a cephalosporin derivative represented by the general formula (XI),

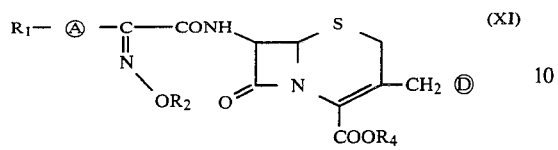

wherein $R_1$, Ⓐ, $R_2$ and $R_4$ have the same meaning as defined before and Ⓓ represents a leaving group, with a compound selected from the group consisting of:

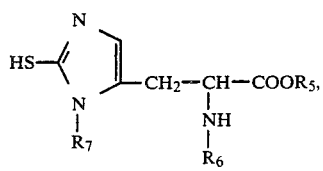

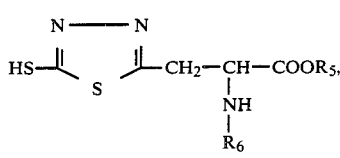

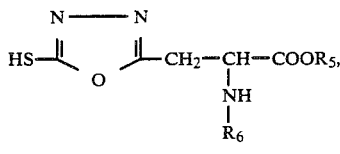

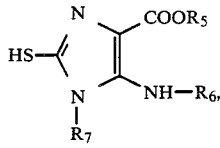

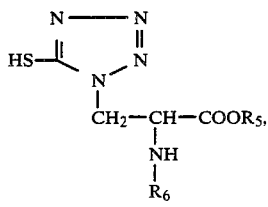

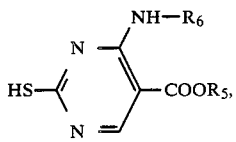

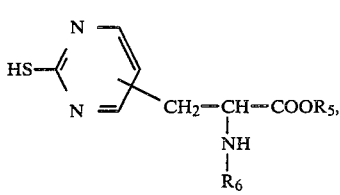

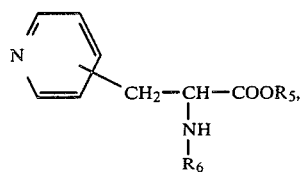

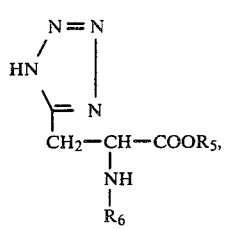

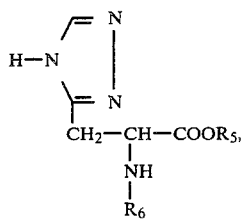

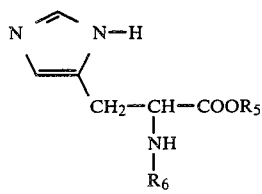

and

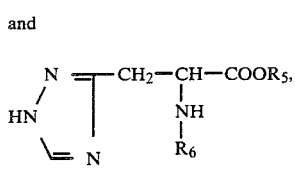

wherein $R_5$, $R_6$ and $R_7$ have the same meaning as defined before.

Further, the preferable second route is a process for preparing a cephalosporin derivative which comprises reacting a cephalosporin compound represented by the general formula (XII),

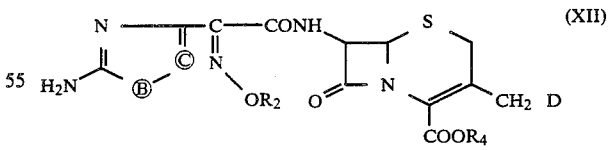

wherein each of Ⓑ, Ⓒ, $R_2$ and $R_4$ represents the same meaning as defined before and Ⓓ represents $-OCOR_8$ (wherein $R_8$ represents an alkyl group having 1 to 6 carbon atoms or a halogen atom), with a compound selected from the above-described group. With reference to the case of using, for example, 2-mercapto-5-(2-amino-2-carboxy)ethyl-1,3,4-thiadiazole as an intermediate for the moiety at the 3-position, this route can be shown by the following equation:

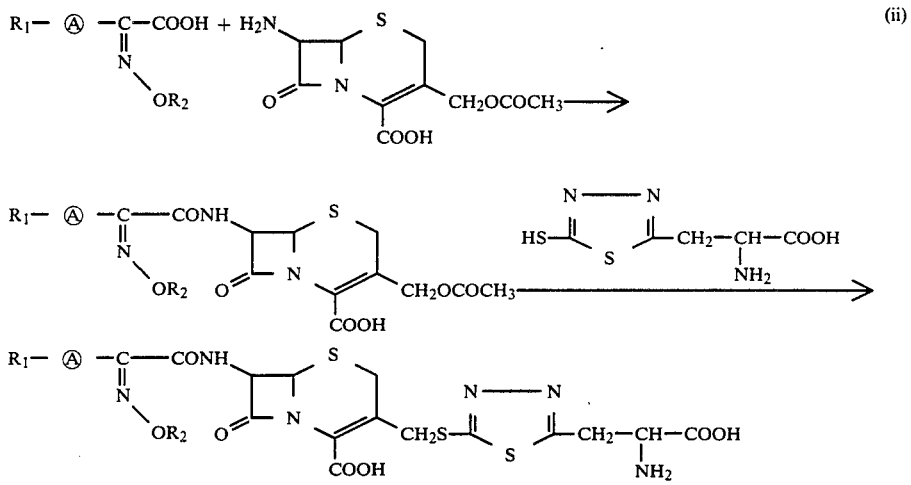
(ii)

In the reaction route (ii), 7-aminocephalosporanic acid is reacted with

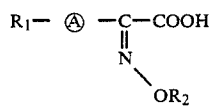

in the presence of a suitable condensation reagent, for example, N,N'-dicyclohexylcarbodiimide. Alternatively,

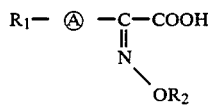

is converted into an active form thereof, e.g., an activated ester, a mixed acid anhydride, etc. followed by reacting with 7-aminocephalosporanic acid. Further, the starting material is converted into an acid chloride thereof such as

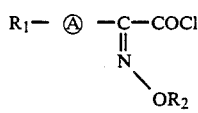

followed by reacting with 7-aminocephalosporanic acid. In the condensation as described above, organic solvents which do not take part in the reaction are chosen; examples of such solvents include tetrahydrofuran, dioxane, ethyl acetate, dimethylformamide, methylene chloride, acetone, etc. Further in the reaction of the acid chloride, it is also possible to use an aqueous system.

In these reactions, the 7-aminocephalosporanic acid can be used in an amount of 1 to 3 mols per mol of

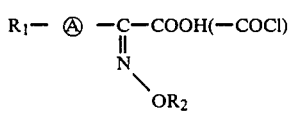

The reaction temperature is generally in the range of $-20°$ to 50° C., preferably $-10°$ to 30° C. The reaction time is in the range of 10 minutes to 20 hours.

Nextly, the reaction for converting the acetoxymethyl group at the 3-position with 2-mercapto-5-(2-amino-2-carboxy)ethyl-1,3,4-thiadiazole can be carried out at temperature ranging from 30° to 100° C. for 1 to 20 hours, preferably 2 to 10 hours in a solvent mixture of water, and/or methanol, and/or acetone using as a base sodium hydrogencarbonate, triethylamine, etc. while controlling pH of the reaction system to about 6 to about 7. During the reaction, it is desired that the reaction system will be kept in a nitrogen atmosphere. Upon this reaction, it is also possible to carry out the reaction using alkali iodides such as sodium iodide, potassium iodide or the like, as an additive.

In addition, especially the following compounds can also be prepared by synthesis routes as shown below.

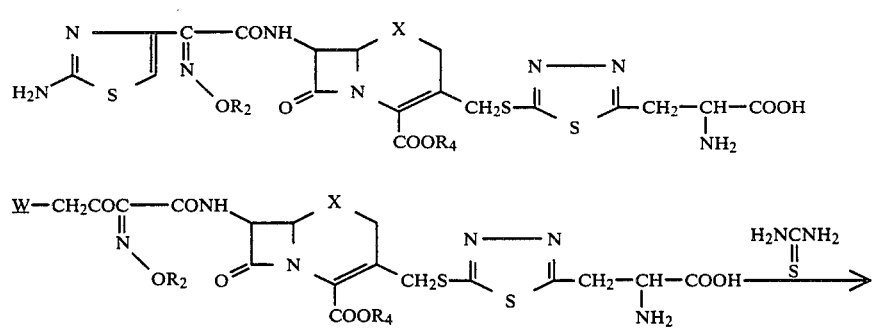

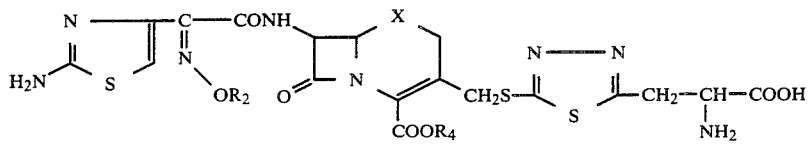

wherein W represents a halogen atom; and $R_2$, $R_4$ and X have the same meaning as defined before.

The cephalosporin compounds according to the present invention exhibit excellent antibacterial activity against both gram-positive bacteria and gram-negative bacteria. Furthermore, they possess superior features in improved intestinal absorption thereof, and high blood concentration and longer biological half-life, to those antibiotic compounds commercially available heretofore.

Details of the preparation of the compounds according to the present invention are explained with reference to the examples below. However, they are included merely to aid the understanding of the invention, and are not to be construed to limit the scope of the present invention.

EXAMPLE 1

Preparation of Compound No. 7

To 20 ml of thionyl chloride was added 5 g of 2-methoxyimino-2-(2-chloroacetylamido-4-thiazolyl)acetic acid and the reaction was carried out at 40° C. for 30 minutes. After completion of the reaction, thionyl chloride was removed by distillation under reduced pressure and the residue was dissolved in 20 ml of acetone. Then, the acid chloride obtained above was dropwise added to a solution of 6 g of 7-aminocephalosporanic acid and 4.8 g of sodium hydrogencarbonate in 30 ml of water and 5 ml of acetone at 5° to 10° C. while maintaining pH to 7 and, stirring was performed for 40 minutes. After completion of the reaction, pH of the reaction liquid was adjusted to 2 with 6N hydrochloric acid. Thereafter, acetone was removed by distillation and water was partly removed by further distillation. After concentration, purification was carried out using a column of synthetic adsorbent, Amberlite XAD-II (hereinafter abbreviated simply as "XAD-II"), to obtain 3.9 g of 7β-[(Z)-2-(2-chloroacetamido-4-thiazolyl)-2-(methoxyimino)acetamido]cephalosporanic acid. Then the product was dissolved in 30 ml of water and 1 g of thiourea was added to the solution. The mixture was stirred for 6 hours at 20° C. to remove the chloroacetyl group. The product was isolated and purified from the reaction liquid using a column of XAD-II.

To 50 ml of water were added 1.5 g of the thus obtained 7β-[(Z)-2-(2-amino-4-thiazolyl)-2-(methoxyimino)acetamido]cephalosporanic acid, 0.7 g of sodium hydrogencarbonate and 0.9 g of 2-mercapto-5-(2-amino-2-carboxy)ethyl-1,3,4-thiadiazole. The mixture was allowed to react at 65° C. for 4 hours in a nitrogen atmosphere while controlling pH to 6.2–6.5. After completion of the reaction, pH of the reaction mixture was adjusted to 2 with 6N hydrochloric acid. After concentration, purification was carried out using a column of XAD-II to give 0.9 g of 7β-[(Z)-2-(2-amino-4-thiazolyl)-2-methoxyimino)acetamido]-3-[5-(2-amino-2-carboxy)ethyl-1,3,4-thiadiazol-2-ylthiomethyl]-3-cephem-4-carboxylic acid.

Reaction Scheme

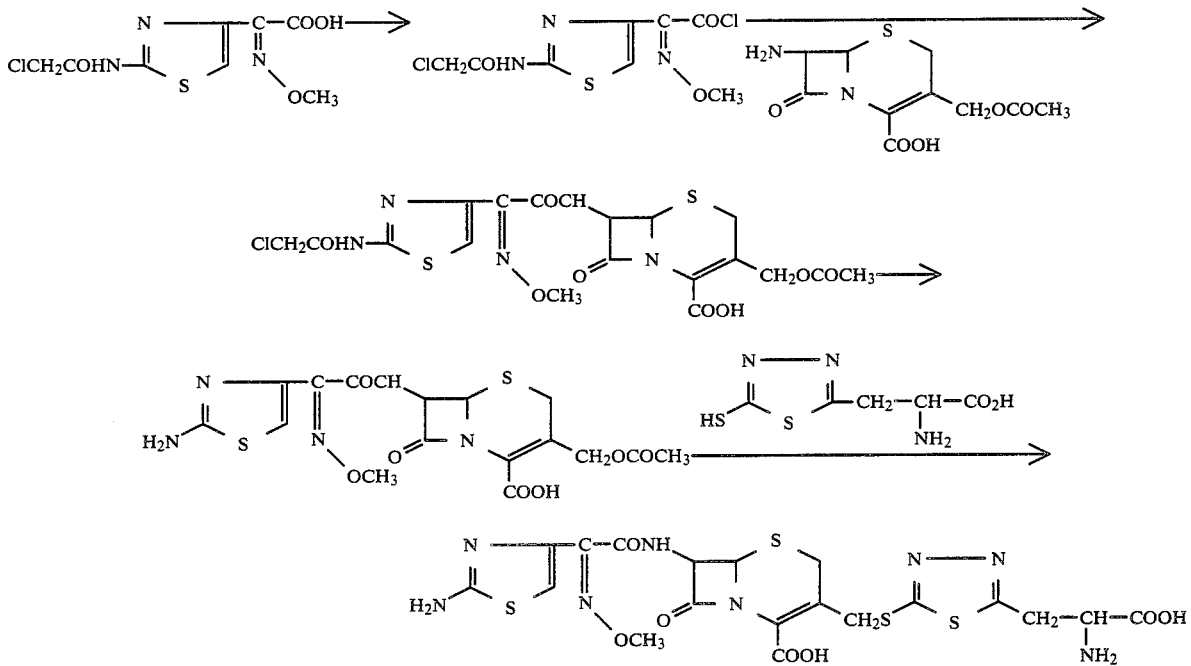

The product was identified, by the NMR spectrum (DMSO-$d_6$ and trifluoroacetic acid were used), as Compound No. 7

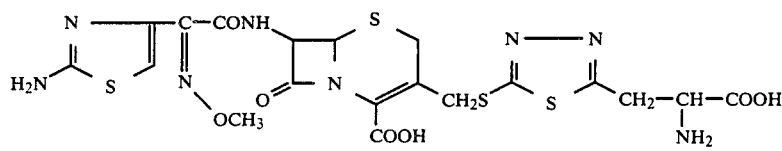

NMR Spectrum (in DMSO-d6 and trifluoroacetic acid)

| 7.03 ppm | 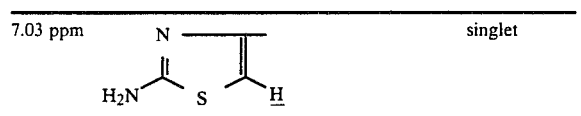 | singlet | hours in a nitrogen atmosphere while controlling pH to 6.2–6.5. After completion of the reaction, pH of the reaction mixture was adjusted to 2 with 6N hydrochloric acid. After concentration, purification was carried out using a column of XAD-II to give 0.9 g of 7β-[(Z)-2-(2-amino-4-thiazolyl)-2-methoxyimino)acetamido]-3-[3-(2-amino-2-carboxy)ethyl-1-pyridium methyl]-3-cephem-4-carboxylic acid.

Reaction Scheme

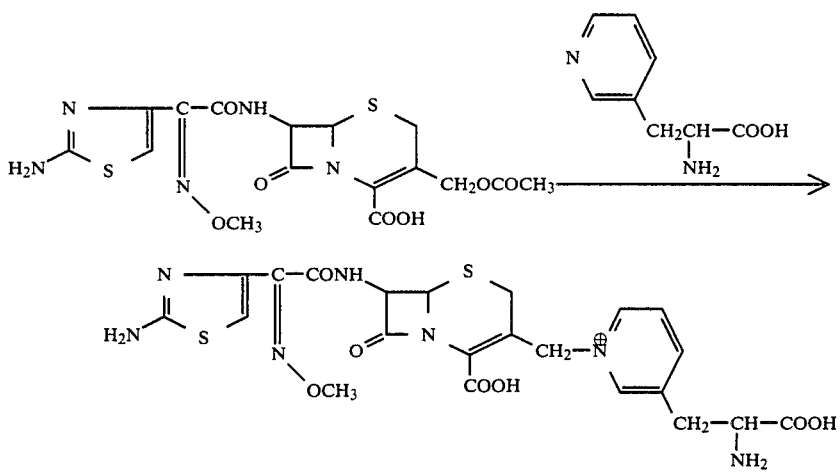

| 5.83 ppm | H-7 | doublet |
| 5.21 ppm | H-6 | doublet |
| 4.43 ppm | —CH2S— | multiplet |
| 4.04 ppm | (structure) | singlet |
| 3.70 ppm | (structure) | doublet |
| 3.68 ppm | (structure) | multiplet |

EXAMPLE 2

Preparation of Compound Nos. 15 and 14

To 50 ml of water were added 1.5 g of the thus obtained 7β-[(Z)-2-amino-4-thiazolyl)-2-(methoxyimino)acetamido]cephalosporanic acid as obtained in Example 1, 0.7 g of sodium hydrogencarbonate, 0.8 g of 3-(2-amino-2-carboxy)ethylpyridine and 1 g of sodium iodide. The mixture was allowed to react at 65° C. for 4

The product was identified, by the NMR spectrum (measured in D2O), as Compound No. 15.

| NMR Spectrum (in D2O) | | |
|---|---|---|
| 8.86 ppm | 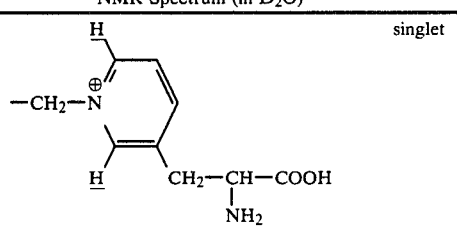 | singlet |
| 8.46 ppm | 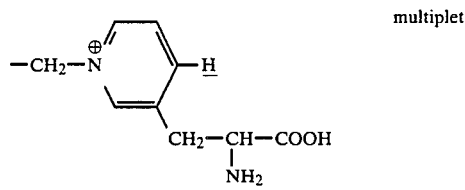 | multiplet |

| NMR Spectrum (in D₂O) | | |
|---|---|---|
| 8.00 ppm | —CH₂—N⁺(pyridine ring with H)—CH₂—CH(NH₂)—COOH | multiplet |
| 6.92 ppm | H₂N—C(=N)—S—CH=C(H)—N—OCH₃ | singlet |
| 5.80 ppm | H-7 | doublet |
| 5.42 ppm | —CH₂—N⁺(pyridine)—CH₂—CH(NH₂)—COOH | multiplet |
| 5.21 ppm | H-6 | doublet |
| 3.93 ppm | H₂N—C(=N)—S—CH=C(H)—N—OCH₃ | singlet |
| 3.41 ppm | β-lactam with S, CH, COOH | multiplet |
| 3.38 ppm | —CH₂—N⁺(pyridine)—CH₂—CH(NH₂)—COOH | multiplet |

Further the following compound was obtained in quite the same manner except that 4-(2-amino-2-carboxy)ethylpyridine was used in place of 3-(2-amino-2-carboxy)ethylpyridine.

The product was identified by the NMR spectrum (measured in D₂O) as Compound No. 14.

| NMR Spectrum (in D₂O) | | |
|---|---|---|
| 8.83 ppm | —CH₂—N⁺(4-pyridine)—CH₂—CH(NH₂)—COOH | doublet |
| 7.96 ppm | —CH₂—N⁺(4-pyridine)—CH₂—CH(NH₂)—COOH | doublet |
| 6.94 ppm | H₂N—C(=N)—S—CH=C(H)—N—OCH₃ | singlet |
| 5.80 ppm | H-7 | doublet |
| 5.39 ppm | —CH₂—N⁺(pyridine)—CH₂—CH(NH₂)—COOH | multiplet |
| 5.20 ppm | H-6 | doublet |
| 4.10 ppm | —CH₂—N⁺(pyridine)—CH₂—CH(NH₂)—COOH | multiplet |
| 3.93 ppm | H₂N—C(=N)—S—CH=C(H)—N—OCH₃ | singlet |
| 3.43 ppm | —CH₂—N⁺(pyridine)—CH₂—CH(NH₂)—COOH | multiplet |
| 3.40 ppm | β-lactam with S, CH, COOH | multiplet |

EXAMPLE 3

Preparation of Compound No. 16

To 150 ml of an aqueous solution obtained by dissolving 1.3 g of 3-(2-amino-2-carboxy)ethylpyridine and Compound No. 14

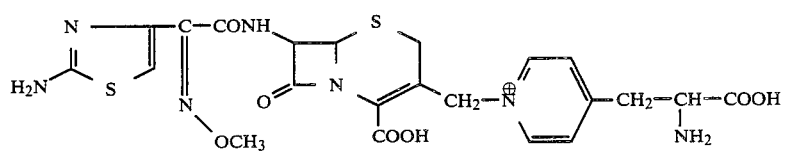

4.6 g of sodium hydrogencarbonate was added 3.5 g of 7β-[(Z)-2-(2-aminothiazol-4-yl)-2-(2-carboxyprop-2-oxyimino)acetamido]cephalosporanic acid and the reaction was performed at 65° C. for 5 hours in a nitrogen atmosphere, whereby pH of the reaction liquid was controlled to 6.3–6.8. After completion of the reaction, water was partly removed by distillation. After concentration, isolation and purification were performed by column chromatography using XAD-II to obtain 1.7 g of the product.

The product was identified by the NMR spectrum (measured in D₂O) as Compound No. 16.

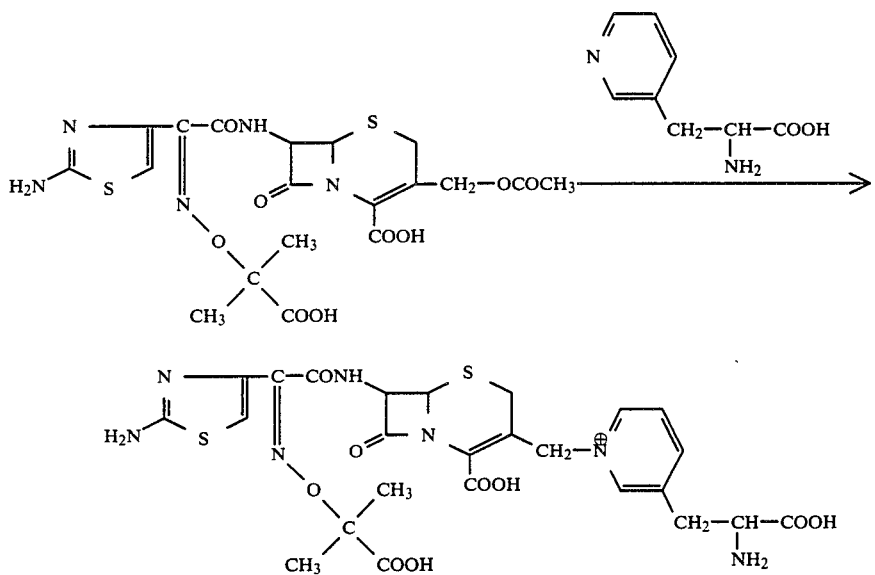

| NMR Spectrum (in D₂O) | | |
|---|---|---|
| 8.87 ppm | [pyridinium CH₂ structure with H, CH₂—CH—COOH, NH₂] | singlet |
| 8.44 ppm | [pyridinium CH₂ structure with H, CH₂—CH—COOH, NH₂] | multiplet |
| 8.00 ppm | [pyridinium CH₂ structure with H, CH₂—CH—COOH, NH₂] | multiplet |

| NMR Spectrum (in D₂O) continued | | |
|---|---|---|
| 6.98 ppm | [aminothiazole oxyimino structure with H₂N, S, N, CH₃, CH₃, COOH] | singlet |
| 5.80 ppm | H-7 | doublet |
| 5.40 ppm | [—CH₂—N⁺ pyridinium with CH₂—CH—COOH, NH₂] | multiplet |
| 5.21 ppm | H-6 | doublet |
| 3.43 ppm | [β-lactam S ring structure with H, H, O, N, COOH] | multiplet |
| 3.34 ppm | [—CH₂—N⁺ pyridinium with CH₂—CH—COOH, NH₂] | multiplet |
| 1.60 ppm | H₃C—C(COOH)—CH₃ | singlet |

EXAMPLE 4

Preparation of Compound No. 9

After dissolving 3.0 g of 7β-[(Z)-2-(2-amino-4-thiazolyl)-2-carboxymethoxyimino)acetamido]-3-acetoxymethyl-3-cephem-4-carboxylic acid, 1.6 g of 2-mercapto-5-(2-amino-2-carboxy)ethyl-1,3,4-thiadiazole and 4.5 g of sodium hydrogencarbonate into 70 ml of water and, the reaction was performed at 65° C. for 5 hours in a nitrogen atmosphere, whereby pH of the reaction liquid was controlled to 6.3–6.7. After completion of the reaction, water was partly removed by distillation. After concentration, isolation and purification were performed by column chromatography using XAD-II to obtain 1.4 g of the product.

Reaction Scheme

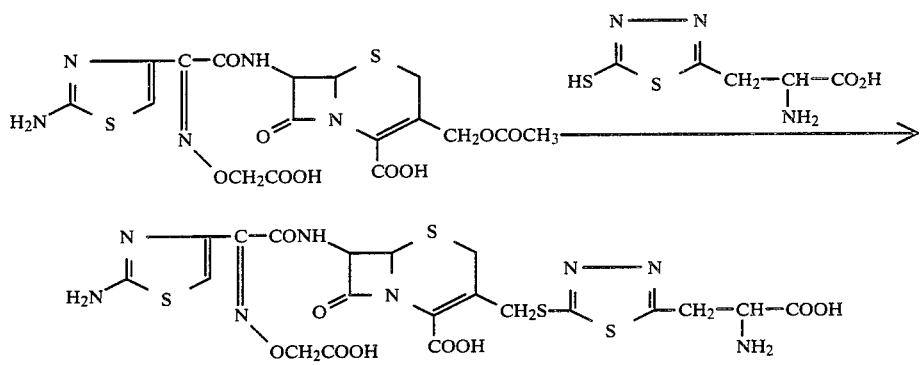

The product was identified by the NMR spectrum (DMSO-D6 was used), as Compound No. 9.

| NMR (in DMSO-d₆) | | |
|---|---|---|
| 9.56 ppm | —CONH— | doublet |
| 6.92 ppm | (thiazole ring with H₂N, S, H) | singlet |
| 5.73 ppm | H-7 | multiplet |
| 5.13 ppm | H-6 | doublet |
| 4.63 ppm | (thiazole with OCH₂—COOH) | singlet |
| 4.33 ppm | (cephem ring with CH₂S, COOH) | multiplet |
| 3.63 ppm | (cephem ring with H, CH₂—S, COOH) | multiplet |
| 3.60 ppm | —CH₂S—(thiadiazole)—CH₂—CH(NH₂)—COOH | multiplet |

EXAMPLE 5

Preparation of Compound No. 8

In a nitrogen atmosphere, 150 ml of an aqueous solution of 3.5 g of 7β-[(Z)-2-(2-amino-4-thiazolyl)-2-(2-carboxyprop-2-oxyimino)acetamido]cephalosporanic acid, 1.8 g of 2-mercapto-5-(2-amino-2-carboxy)ethyl-1,3,4-thiadiazole and 4.6 g of sodium hydrogencarbonate was allowed to react at 65° C. for 5 hours. During the reaction, pH of the reaction liquid was controlled to 6.3–6.8. After completion of the reaction, water was partly removed by distillation. After concentration followed by isolation and purification by column chromatography using XAD-II, 2.1 g of the product was obtained.

Reaction Scheme

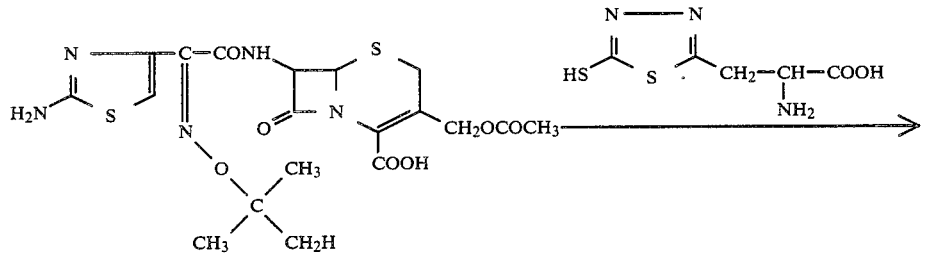

Reaction Scheme

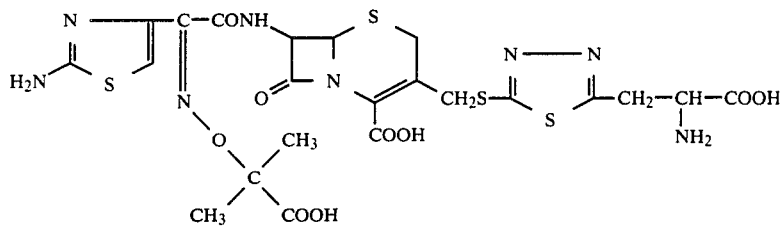

The product was identified, by the NMR spectrum (DMSO-d₆ and trifluoroacetic acid were used), as Compound No. 8.

| NMR Spectrum (in DMSO-d₆ and trifluoroacetic acid) | | |
|---|---|---|
| 7.02 ppm | (structure) | singlet |
| 5.82 ppm | H-7 | doublet |
| 5.18 ppm | H-6 | doublet |
| 4.31 ppm | (structure) | multiplet |
| 3.70 ppm | (structure) | multiplet |
| 3.67 ppm | (structure) | multiplet |
| 1.63 ppm | $H_3C-\underset{COOH}{\underset{|}{C}}-CH_3$ | singlet |

EXAMPLE 6

Preparation of Compound No. 17

After dissolving 3.0 g of 7β-[(Z)-2-(2-amino-4-thiazolyl)-2-carboxymethoxyimino)acetamido]-3-acetoxymethyl-3-cephem-4-carboxylic acid, 1.3 g of 4-(2-amino-2-carboxy)ethylpyridine and 4.5 g of sodium hydrogencarbonate in 70 ml of water, the solution was allowed to react at 65° C. for 5 hours in a nitrogen atmosphere. During the reaction, pH of the reaction liquid was controlled to 6.3–6.7. After completion of the reaction, water was partly removed by distillation. After concentration followed by isolation and purification through column chromatography using XAD-II, 0.8 g of the product was obtained.

Reaction Scheme

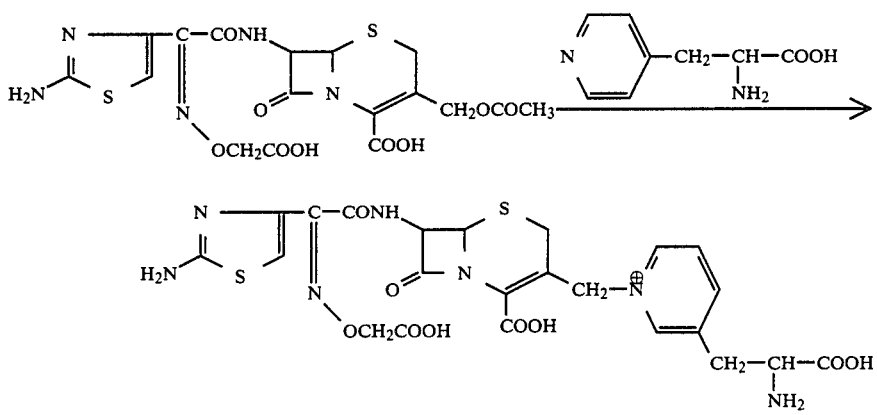

The product was identified, by the NMR spectrum (measured in D₂O), as Compound No. 17.

| NMR Spectrum (in D₂O) | | |
|---|---|---|
| 8.92 ppm | (pyridinium CH₂–N⁺, CH₂–CH(NH₂)–COOH) | doublet |
| 7.93 ppm | (pyridinium CH₂–N⁺, CH₂–CH(NH₂)–COOH) | doublet |
| 6.93 ppm | (H₂N–C(=N)–S–CH=) | singlet |
| 5.76 ppm | H-7 | doublet |
| 5.40 ppm | (CH₂–N⁺, CH₂–CH(NH₂)–COOH) | multiplet |
| 5.21 ppm | H-6 | doublet |
| 4.57 ppm | (H₂N–C(=N)–S–C=N–OCH₂COOH) | singlet |
| 3.47 ppm | (CH₂–N⁺, CH₂–CH(NH₂)–COOH) | multiplet |
| 3.41 ppm | (β-lactam H, S, COOH) | multiplet |

EXAMPLE 7

Preparation of Compound No. 2

2-Mercapto-4-amino-5-carboxy-N-methylimidazole:

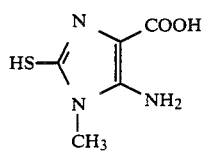

constituting a moiety at the 3-position was synthesized in accordance with the following procedures.

In 20 ml of glacial acetic acid, 11 g of ethyl cyanoacetate was dissolved and the solution was cooled to about 5° C. A solution of 8.7 g of sodium nitrite in 20 ml water was dropwise added to the solution described above over 30 minutes while stirring. The temperature was controlled to about 20° C. during the reaction. After continuing the reaction for further 1 hour, water was poured into the reaction liquid and stirring was then performed to 20° C. for 2 hours. The resulting solution was extracted with 50 ml each of an ether 3 times. The ether solution was washed with a saturated sodium hydrogencarbonate solution and a saturated saline solution followed by drying over anhydrous sodium sulfate. Removal of the ether by distillation gave 12 g of white crystals. Then, the crystals were dissolved in a solvent mixture of 120 ml of formic acid and 50 ml of water and the solution was cooled on an ice bath. To the solution described above, 12 g of zinc powders were added over 10 minutes. The mixture was allowed to react at about 5° C. for 3 hours. Thereafter, the reaction solution was concentrated to about ¼ by volume under reduced pressure. The resulting solution was extracted 5 times with 50 ml each of ether and the ether solution was dried over anhydrous sodium sulfate. After removing the ether and formic acid by distillation, 7.2 g of crystals were obtained. The crsytals were added to 15 ml of ether, and 7.2 g of methyl isothiocyanate dissolved in 10 ml of ether was added thereto while stirring. A homogeneous reaction solution was obtained and allowed to stand at 20° C. for 2 days. The reaction solution was concentrated to about ½ by volume. After allowing to stand, crystals precipitated out and were taken out by filtration to give 4.8 g of the product. Nextly, the product was suspended in 50 ml of a 10% aqueous sodium hydrogencarbonate solution the suspension was boiled under reflux while stirring to give a homogeneous solution. The reaction was continued for further 1 hour followed by cooling. After separating insoluble matters by filtration, the product was separately taken out from the filtrate using a column filled up with XAD-II resin to give 2.5 g of 2-mercapto-4-amino-5-carboxy-N-methylimidazole.

Reaction Scheme

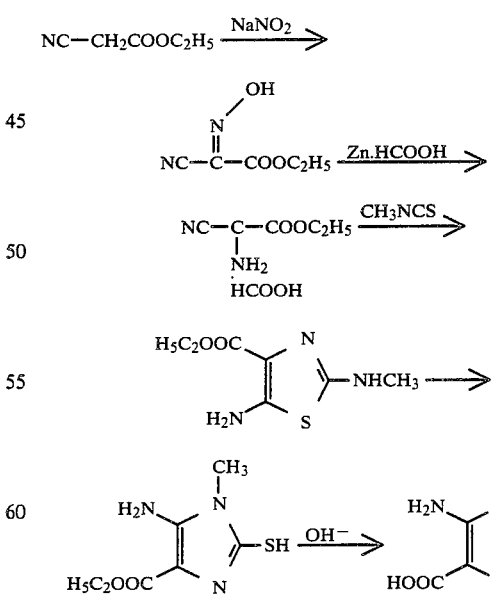

Then, 1.5 g of 7β-[(Z)-2-(2-amino-4-thiazolyl)-2-(methoxyimino)acetamido]cephalosporanic acid obtained in Example 1, 1.0 g of sodium hydrogencarbonate and 0.9 g of 2-mercapto-4-amino-5-carboxy-N- methylimidazole obtained in the above procedures were added to 50 ml of water and the reaction was carried out at 65° C. for 5 hours in a nitrogen atmosphere while controlling pH of 6.00–6.7. After completion of the reaction, pH was adjusted to 2 to 3 with 1N hydrogen chloride. After concentration, purification was carried out using a column of XAD-II. Thus, 0.8 g of 7β-[(Z)-2-(2-amino-4-thiazolyl)-2-(methoxyimino)acetamido]-3-[4-amino-5-carboxy-N-methylimidazol-2-ylthiomethyl]-3-cephem-4-carboxylic acid was obtained.

| NMR (in DMSO—d₆) | | |
|---|---|---|
| 3.63 ppm | (structure) | multiplet |
| 3.24 ppm | | singlet |

Reaction Scheme

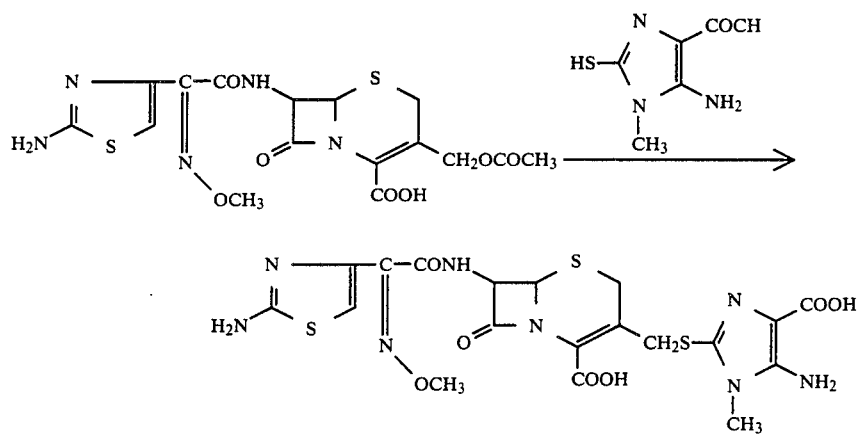

The product was identified by the NMR spectrum (DMSO-D6 was used), as Compound No. 2.

| NMR (in DMSO—d₆) | | |
|---|---|---|
| 9.60 ppm | —CONH— | doublet |
| 7.20 ppm | (structure) | singlet |
| 6.76 ppm | (structure) | singlet |
| 5.76 ppm | H—7 | multiplet |
| 5.10 ppm | H—6 | doublet |
| 4.00 ppm | (structure) | multiplet |
| 3.84 ppm | (structure) | singlet |

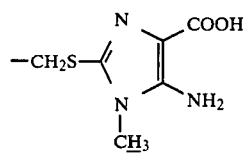

EXAMPLE 8

Preparation of Compound No. 3

In quite the same manner as in Example 7, 3.1 g of 2-mercapto-4-amino-5-carboxy-N-ethylimidazole was obtained except that 8.6 g of ethyl isothiocyanate was used in place of 7.2 g of methyl isothiocyanate in the synthesis of 2-mercapto-4-amino-5-carboxy-N-methylimidazole obtained in Example 7.

Then, 1.5 g of 7β-[(Z)-2-(2-amino-4-thiazolyl)-2-(methoxyimino)acetamido]cephalosporanic acid obtained in Example 1, 1.2 g of sodium hydrogencarbonate and 1.2 g of 2-mercapto-4-amino-5-carboxy-N-ethylimidazole obtained in the above procedures were added to 50 ml of water and the reaction was carried out at 60° to 70° C. for 4 hours in a nitrogen atmosphere while controlling pH to 6.00–6.7. After completion of the reaction, pH was adjusted to 2 to 3 with 1N HCl. After concentration, purification was carried out using a column of XAD-II. Thus, 0.9 g of 7β-[(Z)-2-(2-amino-4-thiazolyl)-2-(methoxyimino)acetamido]-3-[4-amino-5-carboxy-N-ethylimidazol-2-ylthiomethyl]-3-cephem-4-carboxylic acid was obtained.

Reaction Scheme

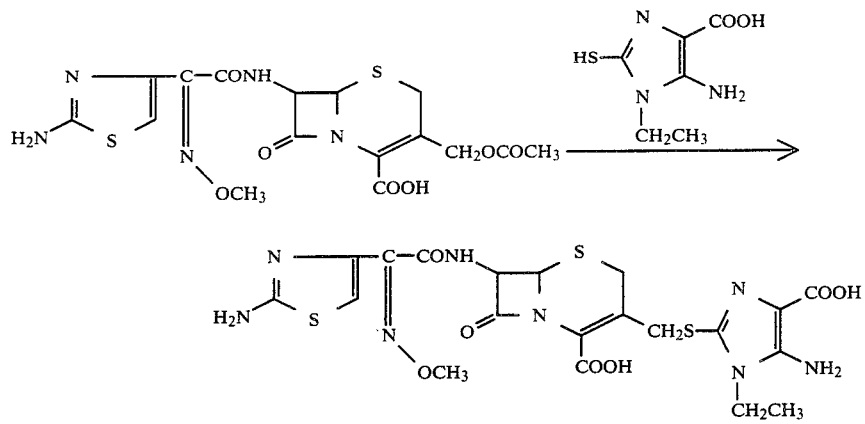

The product was identified, by the NMR spectrum (DMSO-$d_6$ was used), as Compound No. 3.

| NMR (in DMSO—$d_6$) | | |
|---|---|---|
| 9.63 ppm | —CON$\underline{H}$— | doublet |
| 7.23 ppm | ![structure] $H_2N$—thiazole N | singlet |
| 6.77 ppm | ![structure] $H_2N$—thiazole $\underline{H}$ | singlet |
| 5.80 ppm | H—7 | multiplet |
| 5.15 ppm | H—6 | doublet |
| 4.03 ppm | —C$\underline{H_2}$S— imidazole with COOH, NH$_2$, CH$_2$CH$_3$ | multiplet |
| 3.85 ppm | ![structure] thiazole C=N—OCH$_3$ | singlet |
| 3.74 ppm | —C$\underline{H_2}$CH$_3$ | multiplet |
| 3.63 ppm | ![β-lactam structure with $\underline{H}$] | multiplet |
| 1.20 ppm | —CH$_2$C$\underline{H_3}$ | multiplet |

EXAMPLE 9

Preparation of Compound No. 1

To 150 ml of an aqueous solution obtained by dissolving 1.5 g of 2-mercapto-4-amino-5-carboxy-N-methylimidazole as obtained in Example 7 and 4.9 g of sodium hydrogencarbonate was added 3.5 g of 7β-[(Z)-2-(2-amino-4-thiazolyl)-2-(2-carboxyprop-2-oxyimino)acetamido]cephalosporanic acid and the mixture was allowed to react at 65° C. for 5 hours in a nitrogen atmosphere. During the reaction, pH of the reaction liquid was controlled to 6.3–6.8. After completion of the reaction, water was partly removed by distillation. After concentration followed by isolation and purification through column chromatography using XAD-II, 2.1 g of the product was obtained.

Reaction Scheme

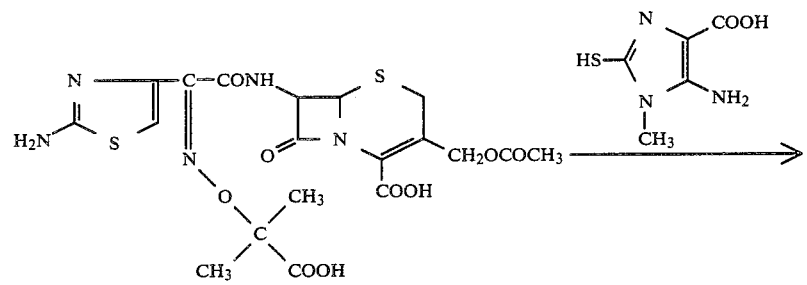

-continued
Reaction Scheme

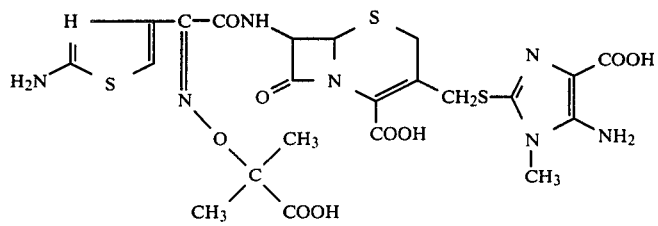

The product was identified by the NMR spectrum (measured in DMSO-d₆) as Compound No. 1.

| NMR (in DMSO—d₆) | | |
|---|---|---|
| 9.59 ppm | —CONH— | doublet |
| 7.18 ppm | H₂N–C(=N)–S–CH= (ring) | singlet |
| 6.80 ppm | H₂N–C(=N)–S–CH (ring with H) | singlet |
| 5.79 ppm | H—7 | multiplet |
| 5.16 ppm | H—6 | doublet |
| 4.06 ppm | —CH₂S—imidazole(COOH, NH₂, N-CH₃) | multiplet |
| 3.63 ppm | β-lactam/cephem ring H,H | multiplet |
| 3.24 ppm | —CH₂S—imidazole(COOH, NH₂, N-CH₃) | singlet |
| 1.60 ppm | CH₃–C(COOH)–CH₃ | singlet |

EXAMPLE 10

Preparation of Compound No. 4

To 50 ml of water were added 1.5 g of 7β-[(Z)-2-(2-amino-4-thiazolyl)-2-(methoxyimino)acetamido]cephalosporanic acid as obtained in Example 1, 1.3 g of 2-mercapto-4-amino-5-ethoxycarbonyl-N-methylimidazole and 1.0 g of sodium hydrogencarbonate, and the mixture was allowed to react at 65° C. for 5 hours in a nitrogen atmosphere, while controlling pH to 6.0–6.7. After completion of the reaction, pH was adjusted to 3 with 1N HCl. After concentration, purification was performed using a column of XAD-II, 0.8 g of the product, 7β-[(Z)-2-(2-amino-4-thiazolyl)-2-(methoxyimino)acetamido]-3-[4-amino-5-ethoxycarbonyl-N-methylimidazol-2-ylthiomethyl]-3-cephem-4-carboxylic acid, was obtained.

Reaction Scheme

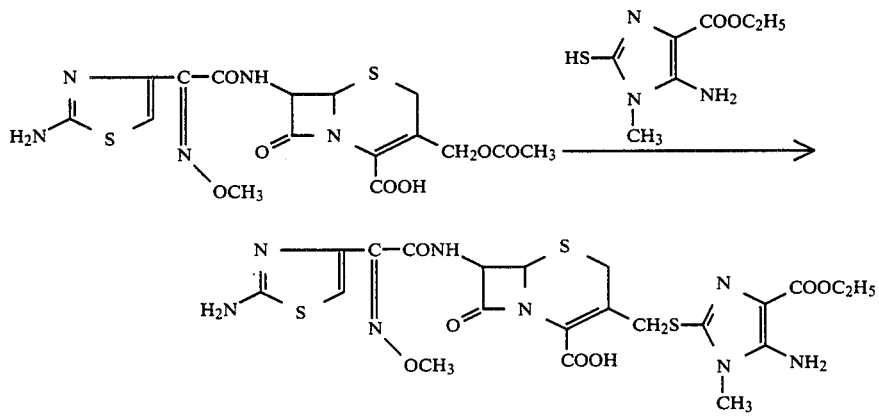

The product was identified by the NMR spectrum (measured in DMSO-d₆) as Compound No. 4.

| NMR (in DMSO—d6) | | |
|---|---|---|
| 9.58 ppm | —CONH— | doublet |
| 7.20 ppm | (thiazole with H2N, N, S) | singlet |
| 6.76 ppm | (thiazole with H2N, N, S, H) | singlet |
| 6.19 ppm | —CH2S—C(=N–CH3)(NH2)=C(COOC2H5) | singlet |
| 5.73 ppm | H—7 | multiplet |
| 5.13 ppm | H—6 | doublet |
| 4.05 ppm | —CH2S—C(=N–CH3)(NH2)=C(COOCH2CH3) | multiplet |
| 4.00 ppm | —CH2S—C(=N–CH3)(NH2)=C(COOCH2CH3) | singlet |
| 3.83 ppm | (aminothiazolyl methoxyimino group) | singlet |
| 3.61 ppm | (β-lactam ring H) | multiplet |

| NMR (in DMSO—d6) | | |
|---|---|---|
| 1.10 ppm | —CH2S—C(=N–CH3)(NH2)=C(COOCH2CH3) | multiplet |

EXAMPLE 11

Preparation of Compound No. 23

To 50 ml of water were added 1.5 g of 7β-[(Z)-2-(2-amino-4-thiazolyl)-2-(methoxyimino)acetamido]cephalosporanic acid as obtained in Example 1, 0.7 g of sodium hydrogencarbonate and 0.8 g of 2-thiol-L-histidine. The mixture was allowed to react at 65° C. for 4 hours in a nitrogen atmosphere while controlling pH to 6–6.5. After completion of the reaction, pH of the reaction mixture was adjusted to 2 with 6N hydrochloric acid. After concentration, purification was carried out using a column of XAD-II to give 0.9 g of 7β-[(Z)-2-(2-amino-4-thiazolyl)-2-methoxyimino)acetamido]-3-[(2-amino-2-carboxy)ethyl-imidazol-2-ylthiomethyl]-3-cephem-4-carboxylic acid.

Reaction Scheme

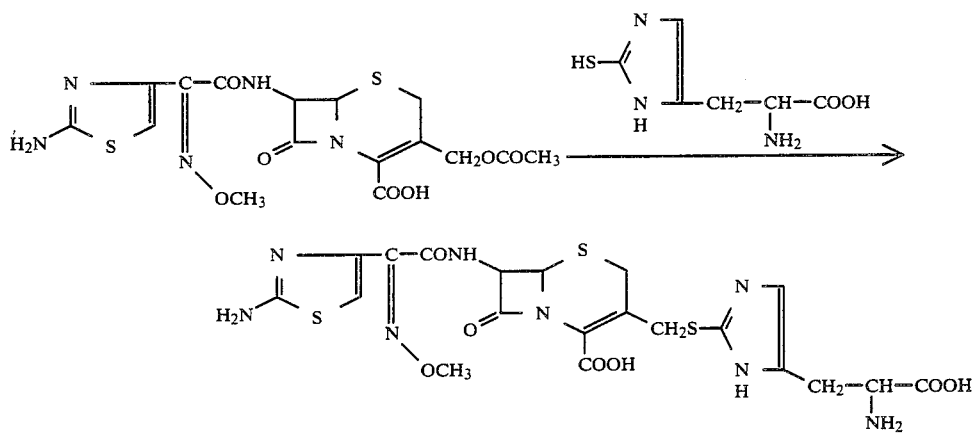

The product was identified, by the NMR spectrum (DMSO-d6 and trifluoroacetic acid were used), as Compound No. 23.

| NMR Spectrum (in DMSO—d6 and trifluoroacetic acid) | | |
|---|---|---|
| 3.46 ppm | (β-lactam ring with S, CH2) | multiplet |
| 4.00 ppm | =C—N—OCH3 | singlet |

-continued

| NMR Spectrum (in DMSO—$d_6$ and trifluoroacetic acid) | | |
|---|---|---|
| 4.46 ppm | | multiplet |
| 5.04 ppm | H—6 | doublet |
| 5.67 ppm | H—7 | doublet |
| 7.09 ppm | | singlet |
| 7.25 ppm | | singlet |

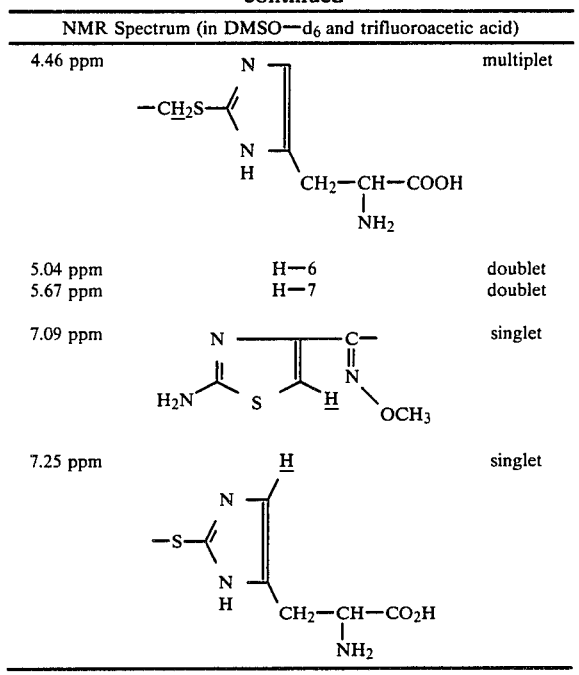

EXAMPLE 12

Preparation of Compound No. 25

To 150 ml of an aqueous solution obtained by dissolving 2.5 g of 2-thiol-L-histidine and 4.6 g of sodium hydrogencarbonate was added 3.5 g of 7β-[(Z)-2-(2-amino-4-thiazolyl)-2-(2-carboxyprop-2-oxyimino)acetamido]cephalosporanic acid, and the reaction was performed at 65° C. for 5 hours in a nitrogen atomsphere. During the reaction, pH of the reaction liquid was controlled to 6–6.8. After completion of the reaction, water was partly removed by distillation. After concentration, isolation and purification were performed by column chromatography using XAD-II to obtain 2.1 g of the product.

The product was identified, by the NMR spectrum (DMSO-$d_6$ and trifluoroacetic acid were used), as Compound No. 25.

| NMR Spectrum (in DMSO—$d_6$ and trifluoroacetic acid) | | |
|---|---|---|
| 1.56 ppm | | singlet |
| 3.22 ppm | | multiplet |
| 3.65 ppm | | multiplet |
| 4.27 ppm | | multiplet |
| 5.11 ppm | H—6 | doublet |
| 5.89 ppm | H—7 | doublet |
| 7.03 ppm | | singlet |

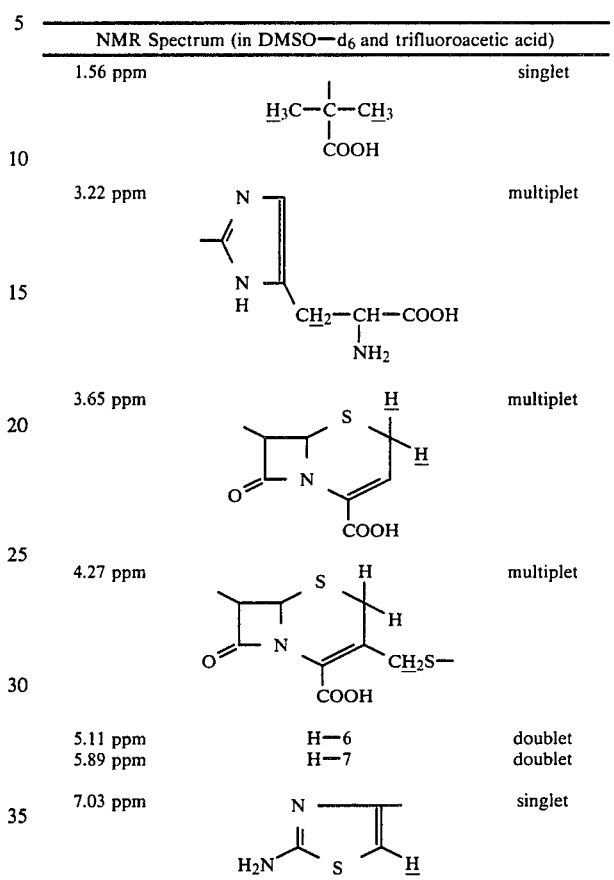

Reaction Scheme

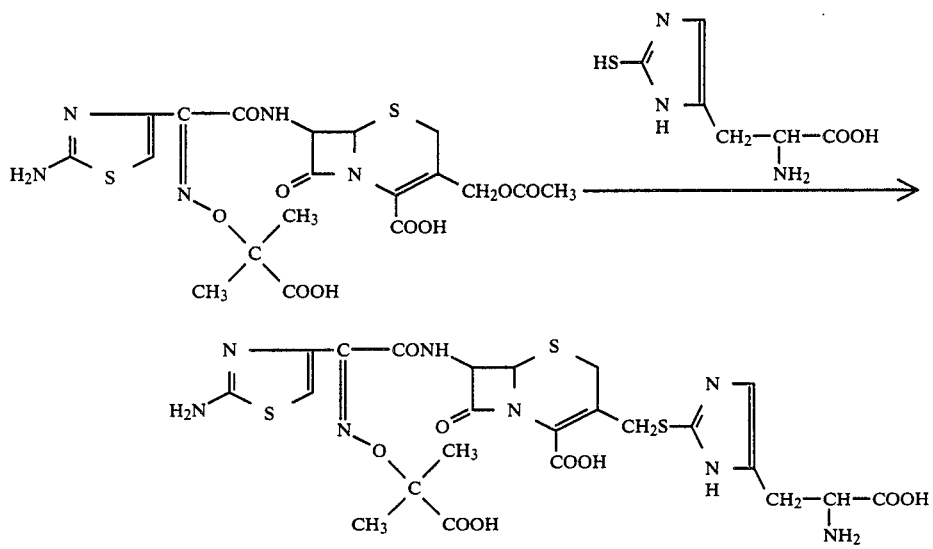

| NMR Spectrum (in DMSO—d₆ and trifluoroacetic acid) | | |
|---|---|---|
| 7.60 ppm | (thiazoline ring with -S-, N, NH, CH₂—CH(NH₂)—CO₂H) | singlet |

EXAMPLE 13

Preparation of Compound No. 26

To 50 ml of water were added 1.5 g of 7β-[(Z)-2-(2-amino-4-thiazolyl)-2-(methoxyimino)acetamido]cephalosporanic acid obtained in Example 1, 0.9 g of sodium hydrogencarbonate and 1.3 g of (2-amino-2-carboxy)ethyl-1,2,3,4-tetrazole and the reaction was performed at 70° C. for 6 hours in a nitrogen atmosphere, while controling pH to 6.0–7.0. After completion of the reaction, isolation and purification were performed using a column of Amberlite XAD-II to obtain 1.0 g of the product.

Reaction Scheme

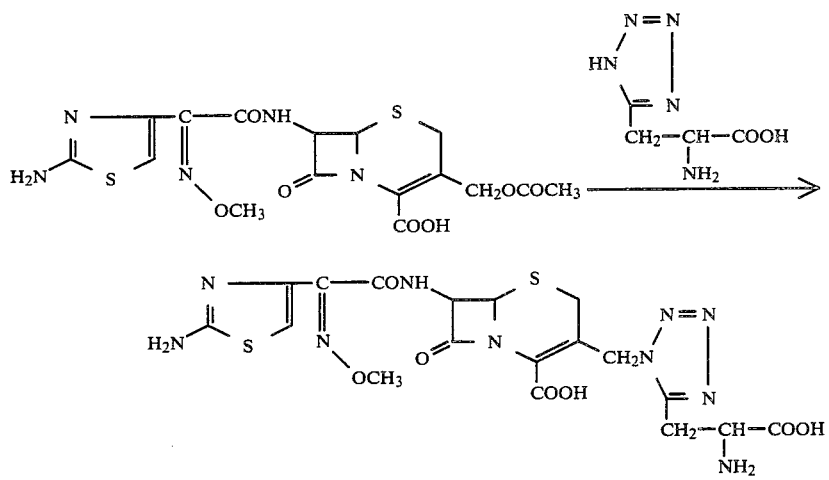

The product was identified, by the NMR spectrum (DMSO-d₆ and trifluoroacetic acid were used), as Compound No. 26.

| NMR Spectrum (in DMSO—d₆ and trifluoroacetic acid) | | |
|---|---|---|
| 7.00 ppm | (aminothiazolyl structure with H₂N, S, N, H) | singlet |
| 5.81 ppm | H—7 | doublet |
| 5.34 ppm | (cephem structure with tetrazole ring, COOH, CH₂N) | multiplet |

| NMR Spectrum (in DMSO—d₆ and trifluoroacetic acid) | | |
|---|---|---|
| 5.24 ppm | H—6 | doublet |
| 4.02 ppm | (structure with H₂N, S, N, OCH₃) | singlet |
| 3.71 ppm | (cephem structure with triazole, COOH, CH₂N, CH₂—CH(NH₂)—COOH) | multiplet |
| 3.66 ppm | (β-lactam structure with S, H, COOH) | multiplet |

EXAMPLE 14

Preparation of Compound No. 30

To 50 ml of water were added 1.5 g of 7β-[(Z)-2-(2-amino-4-thiazolyl)-2-(methoxyimino)acetamido]cephalosporanic acid as obtained in Example 1, 0.9 g of sodium hydrogencarbonate and 1.5 g of (2-amino-2-carboxy)ethyl-1,2,4-triazole and, the reaction was performed at 65° C. for 10 hours in a nitrogen atmosphere, while controling pH to 6.0–7.0. After completion of the reaction, isolation and purification were performed using a column of Amberlite XAD-II to obtain 0.9 g of the product.

Reaction Scheme

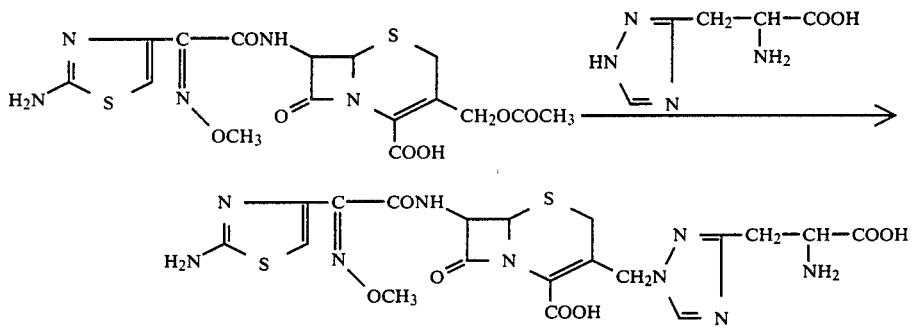

The product was identified, by the NMR spectrum (DMSO-d6 and trifluoroacetic acid were used), as Compound No. 30.

| NMR Spectrum (in DMSO—d6 and trifluoroacetic acid) | | |
|---|---|---|
| 7.02 ppm | (H2N-C(=N)-S-CH=, H) | singlet |
| 5.79 ppm | H—7 | doublet |
| 5.26 ppm | H—6 | doublet |
| 5.12 ppm | (β-lactam fragment with CH2N-pyridine) | multiplet |
| 4.00 ppm | (H2N-C(=N)-S-CH=C-OCH3) | singlet |
| 3.70 ppm | (β-lactam with CH2N-pyridine-CH2-CH(NH2)-COOH) | multiplet |
| 3.62 ppm | (β-lactam S-CH2, H) | multiplet |

EXAMPLE 15

Preparation of Compound No. 14

In 30 ml of 50% dioxane, 2 g of 4-(2-amino-2-carboxy)ethylpyridine was dissolved and 0.8 ml of triethylamine and 3.6 g of 2-tert-butyloxycarbonyloximino-2-phenylacetonitrile were added to the resulting solution. The reaction was carried out at 5° C. for 5 hours. After completion of the reaction, the unreacted 2-tert-butyloxycarbonyloximino-2-phenylacetonitrile was extracted with 20 ml of ethyl acetate to remove the same. After adjusting pH of the aqueous phase to 2 with 1N HCl, the desired product was extracted with ethyl acetate, washed with water, dried over anhydrous magnesium sulfate, concentrated and evaporated to dryness. Thus, 2.4 g of tert-butyloxycarbonylated 4-(2-amino-2-carboxy)ethylpyridine was obtained.

Then, 2.0 g of 7-aminocephalosporanic acid and 2.4 g of the thus obtained tert-butyloxycarbonylated 4-(2-amino-2-carboxy)ethylpyridine were added to 40 ml of water and 20 ml of acetone. While controlling pH to 5.0–6.4, the reaction was carried out at 65° C. for 5 hours. After completion of the reaction, acetone was removed by distillation. Isolation of the desired product by column chromatography using XAD-II gave 2.4 g of the product.

Nextly, the thus obtained product was added to 60 ml of tetrahydrofuran and 2.6 moles of a trimethylsilylating agent of bis(trimethylsilyl)acetamide was added thereto.

Then 1.5 g of 2-(2-tert-butoxycarbonylamino-4-thiazolyl)-2-(methoxyimino)acetic acid and 1.0 g of N,N'-dicyclohexylcarbodiimide were added to 50 ml of tetrahydrofuran, and the resulting mixture was stirred at 20° C. for 2 hours. Thereafter, the tetrahydrofuran solution obtained by the procedure described above was added to the resulting solution and the mixture was stirred at 20° C. for 10 hours. Precipitates were separated by filtration. After adding 10 ml of water to the filtrate, water and tetrahydrofuran were removed by distillation under reduced pressure. The residue was dissolved in 50 ml of formic acid and the reaction was carried out at 10° C. for 2 hours. After removing formic acid by distillation, 20 ml of ether was added. A solid substance precipitated out was taken out and isolated and purified by column chromatography using XAD-II to obtain 1.3 g of the desired product.

Reaction Scheme

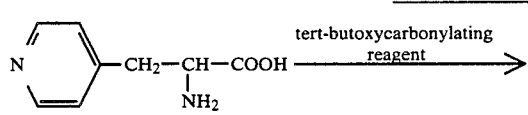

-continued
Reaction Scheme

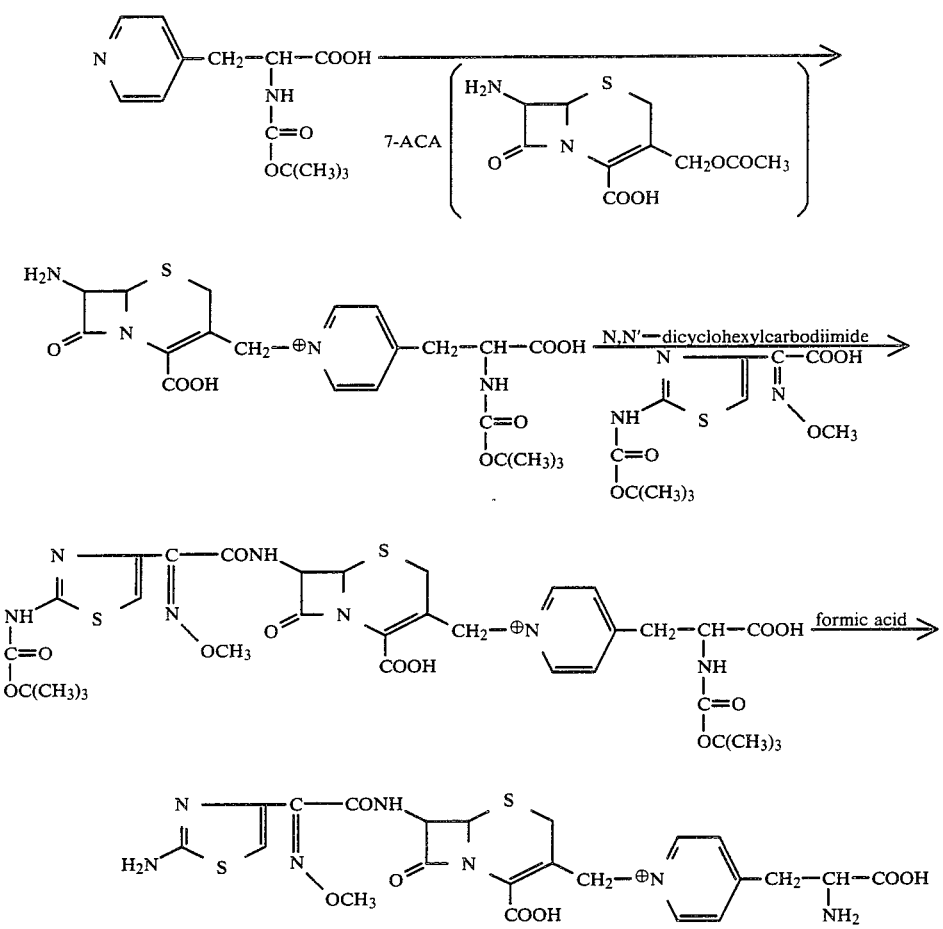

As a result of NMR measurements, the product was all identical with the compound obtained in Example 2, 7β-[(Z)-2-(2-amino-4-thiazolyl)-2-(methoxyimino)acetamido]-3-[4-(2-amino-2-carboxy)ethyl-1-pyridium methyl]-3-cephem-4-carboxylic acid (Compound No. 14).

EXAMPLE 16

Preparation of Compound No. 10

In 50 ml of dimethylsulfoxide, 5.2 g of 2-mercapto-5-(2-amino-2-carboxy)ethyl-1,3,4-thiadiazole was dissolved, and 5.8 g of 1,1,3,3-tetramethylguanidine and 5.4 g of t-butylphenyl carbonate were added to the resulting solution.

The reaction was carried out at 20° C. for 20 hours. After completion of the reaction, 200 ml of water was added and extraction was performed with 100 ml of ethyl acetate. After adjusting pH of the aqueous phase to 2 with 1N HCl, extraction was further performed twice with 100 ml of ethyl acetate. After drying over anhydrous magnesium sulfate, ethyl acetate was removed by distillation to give 4.8 g of the residue.

Then, 3 g of 7-aminocephalosporanic acid and the thus obtained tert-butyloxycarbonylated 2-mercapto-5-(2-amino-2-carboxy)ethyl-1,3,4-thiadiazole were added to 100 ml of water and 50 ml of acetone. Further 3.5 g of sodium hydrogen-carbonate was added thereto. While controlling pH to 6.0–6.5, the reaction was carried out at 65° C. in a nitrogen atmosphere. After reacting for 6 hours, acetone in the reaction liquid was removed by distillation. Isolation by column chromatography using XAD-II gave 2.3 g of the product.

Nextly, 2.3 g of the thus obtained t-butyloxycarbonylated compound of 7-amino-3-[5-(2-amino-2-carboxy)ethyl-1,3,4-thiadiazol-2-ylthiomethyl]-3-cephem-4-carboxylic acid was added to 50 ml of tetrahydrofuran and 2.4 moles of a trimethylsilylating agent of bis(-trimethylsilyl)acetamide was added thereto.

Then 1.7 g of 2-(4-tert-butoxycarbonylamino-2-thiazolyl)-2-(isopropoxyimino)acetic acid and 1.0 g of N,N'-dicyclohexylcarbodiimide were added to 50 ml of tetrahydrofuran and the resulting mixture was stirred at 20° C. for 2 hours. Thereafter, the tetrahydrofuran solution obtained by the procedure described above was added to the resulting solution and the mixture was allowed to react at 20° C. for 10 hours while stirring. Precipitates were separated by filtration. After adding 10 ml of water to the filtrate, water and tetrahydrofuran were removed by distillation under reduced pressure. The residue was dissolved in 40 ml of formic acid and the reaction was carried out at 10° C. for 2 hours. After removing formic acid by distillation, 20 ml of ether was added. A solid substance precipitated out was taken out and isolated and purified by column chromatography using XAD-II to obtain 1.7 g of the desired product.

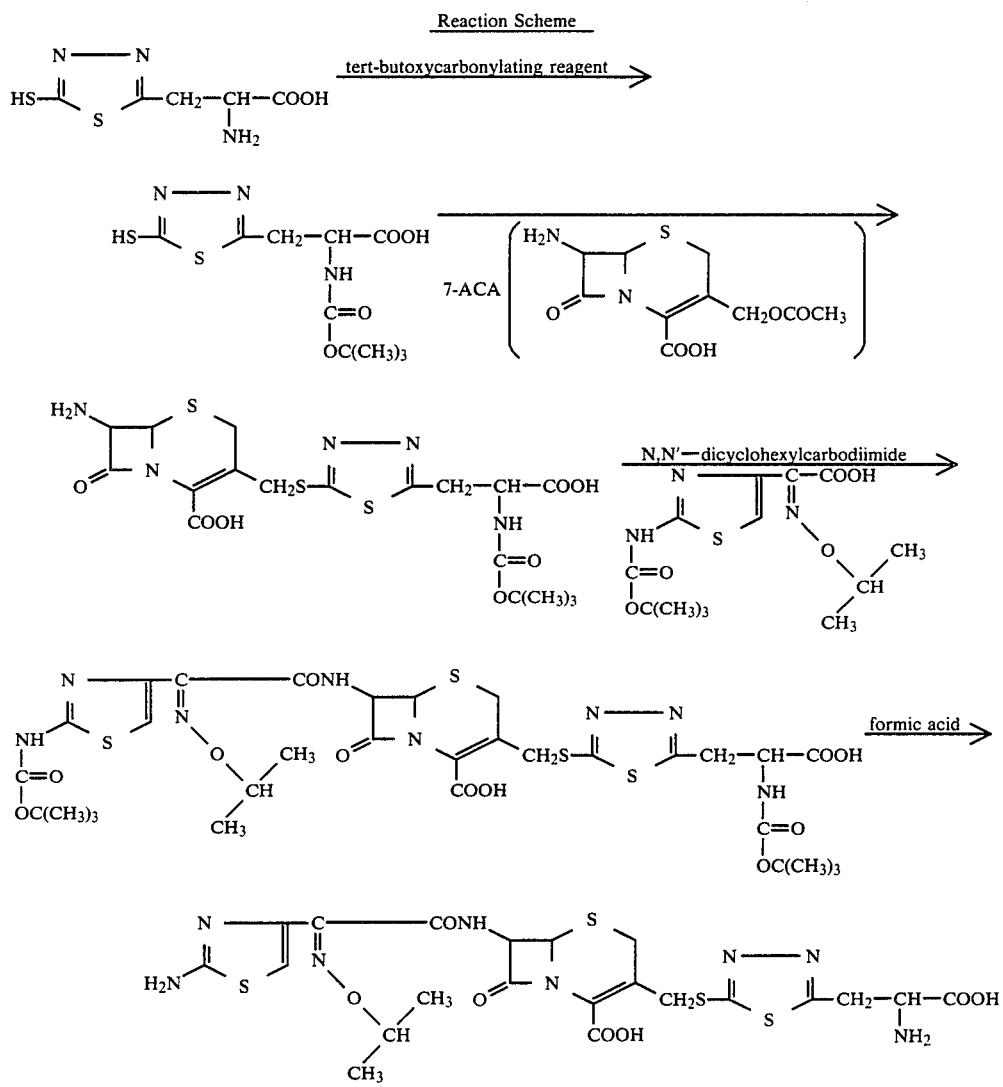

Reaction Scheme

The product was identified, by the NMR spectrum (DMSO-d₆ and trifluoroacetic acid were used), as Compound No. 10.

| NMR Spectrum (in DMSO-d$_6$ and trifluoroacetic acid) | | |
|---|---|---|
| 7.00 ppm | (structure: H$_2$N-C(=N)-S-CH=) | singlet |
| 5.90 ppm | H-7 | doublet |
| 5.26 ppm | H-6 | doublet |
| 4.39 ppm | (β-lactam CH$_2$S– structure) | multiplet |
| 3.81 ppm | (β-lactam H structure) | multiplet |
| 3.31 ppm | (–CH$_2$S–thiadiazole–CH$_2$–CH(NH$_2$)–COOH) | multiplet |
| 1.36 ppm | –O–CH(CH$_3$)$_2$ | singlet |

EXAMPLE 17

Preparation of Compound No. 24

In 50 ml of dimethylsulfoxide, 4.7 g of thiol histidine was dissolved, and 5.8 g of 1,1,3,3-tetramethylguanidine and 5.4 g of t-butylphenyl carbonate were added to the resulting solution. The reaction was carried out at 20° C. for 25 hours.

After completion of the reaction, 200 ml of water was added and extraction was performed with 100 ml of ethyl acetate. After adjusting pH of the aqueous phase to 2 with 1N HCl, extraction was further performed twice with 100 ml of ethyl acetate. After drying over anhydrous magnesium sulfate, ethyl acetate was removed by distillation to give 4.6 g of the residue.

Then, 3 g of 7-aminocephalosporanic acid and 4.6 g of the thus obtained tert-butyloxycarbonylated thiol histidine were added to 100 ml of water and 50 ml of acetone. Furtheo 3.5 g of sodium hydrogencarbonate was added thereto. While controlling pH to 6.0–7.0, the reaction was carried out at 65° C. in a nitrogen atmosphere. After reacting for 6 hours, acetone in the reaction liquid was removed by distillation. Isolation by column chromatography using XAD-II gave 2.3 g of the product.

Nextly, 2.3 g of the thus obtained 7-amino-3-[(2-t-butyloxycarbonylamino-2-carboxy)ethylimidazol-2-ylthiomethyl]-3-cephem-4-carboxylic acid was added to 70 ml of tetrahydrofuran and 3.0 moles of a trimethylsilylating agent of bis(trimethylsilyl)acetamide was added thereto.

Then 1.6 g of 2-(2-tert-butyloxycarbonylamino-4-thiazolyl)-2-(ethoxyimino)acetic acid and 1.1 g of N,N'-dicyclohexylcarbodiimide were added to 50 ml of tetrahydrofuran and the resulting mixture was stirred at 20° C. for 2 hours. Thereafter, the tetrahydrofuran solution obtained by the procedure described above was added to the resulting solution and the mixture was allowed to react at 20° C. for 10 hours while stirring. Precipitates were separated by filtration. After adding 10 ml of water to the filtrate, water and tetrahydrofuran were removed by distillation under reduced pressure. The residue was dissolved in 40 ml of formic acid and the reaction was carried out at 10° C. for 2 hours. After removing formic acid by distillation, 20 ml of ether was added. A solid substance precipitated out was taken out and isolated and purified by column chromatography using XAD-II to obtain 1.6 g of the desired product.

It was confirmed by NMR spectra that the product was 7β-[(Z)-2-(2-amino-4-thiazolyl)-2-(ethoxyimino)acetamido]-3-[(2-amino-2-carboxy)ethylimidazol-2-ylthiomethyl]-3-cephem-4-carboxylic acid (Compound No. 24).

Reaction Scheme

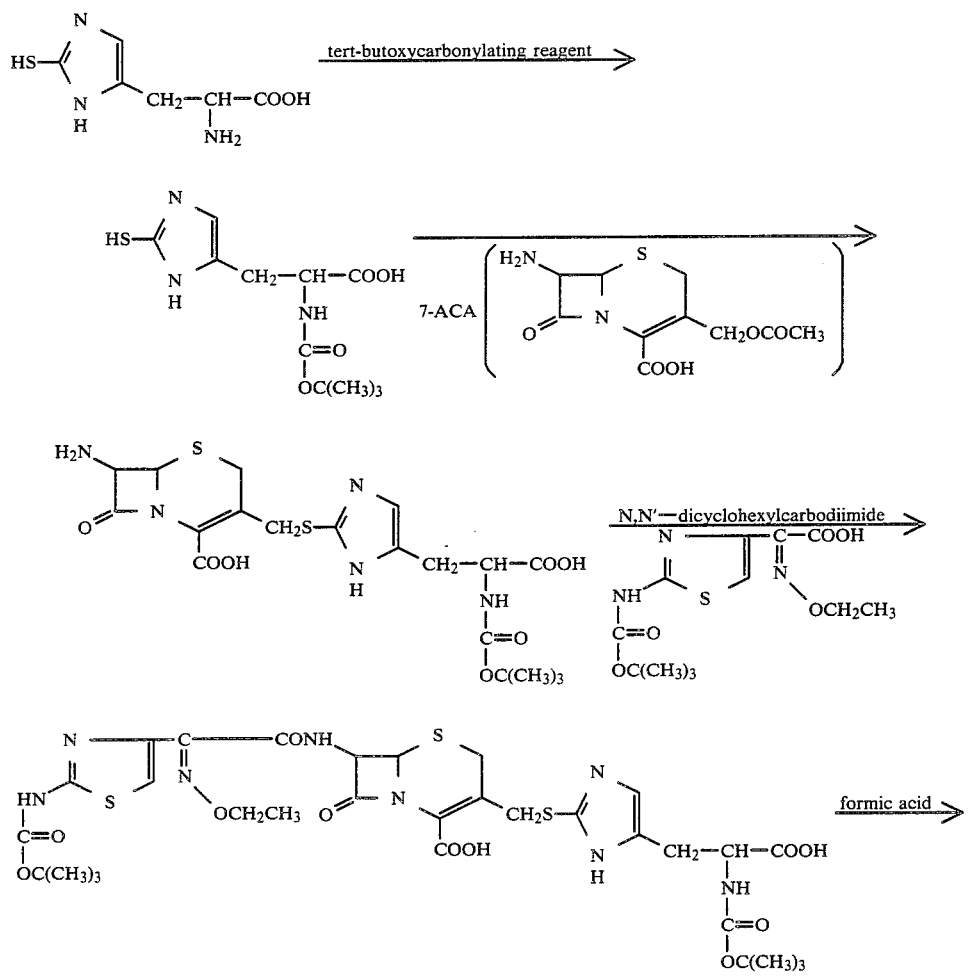

-continued
Reaction Scheme

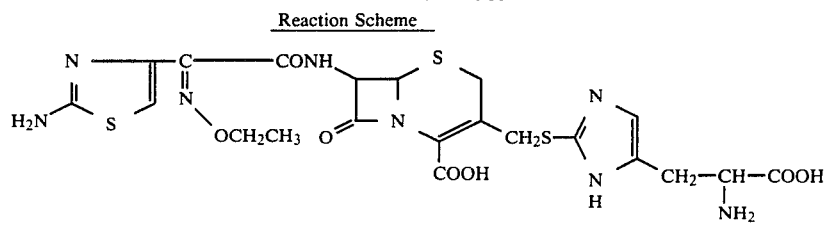

| NMR Spectrum (in DMSO-d₆ and trifluoroacetic acid) | | |
|---|---|---|
| 7.60 ppm | (structure) | singlet |
| 7.02 ppm | (structure) | singlet |
| 5.90 ppm | H-7 | doublet |
| 5.29 ppm | H-6 | doublet |
| 4.37 ppm | —OC$\underline{H}_2$CH₃ | multiplet |
| 4.36 ppm | (structure) | multiplet |
| 3.78 ppm | (structure) | multiplet |
| 3.33 ppm | (structure) | multiplet |
| 1.33 ppm | —OCH₂C$\underline{H}_3$ | multiplet |

EXAMPLE 18

Preparation of Compound No. 21

2.3 g of 7-amino-3-[(2-t-butyloxycarbonylamino-2-carboxy)ethylimidazol-2-ylthiomethyl]-3-cephem-4-carboxylic acid as obtained in Example 17 was added to 70 ml of tetrahydrofuran and 2.5 moles of a trimethylsilylating agent of bis(trimethylsilyl)acetamide was added thereto.

Then 2.0 g of 2-(2-tert-butyloxycarbonylamino-4-thiazolyl)-2-(benzyloxyimino)acetic acid and 1.1 g of N,N'-dicyclohexylcarbodiimide were added to 50 ml of tetrahydrofuran and the resulting mixture was stirred at 20° C. for 2 hours. Thereafter, the tetrahydrofuran solution obtained by the procedure described above was added to the resulting solution and the mixture was allowed to react at 20° C. for 10 hours while stirring. Precipitates were separated by filtration. After adding 10 ml of water to the filtrate, water and tetrahydrofuran were removed by distillation under reduced pressure. The residue was dissolved in 40 ml of formic acid and the reaction was carried out at 10° C. for 2 hours. After removing formic acid by distillation, 20 ml of ether was added. A solid substance precipitated out was taken out and isolated and purified by column chromatography using XAD-II to obtain 1.6 g of the desired product.

It was confirmed by NMR spectra that the product was 7β-[(Z)-2-(2-amino-4-thiazolyl)-2-(benzyloxyimino)acetamido]-3-[(2-amino-2-carboxy)ethylimidazol-2-ylthiomethyl]-3-cephem-4-carboxylic acid (Compound No. 21).

Reaction Scheme

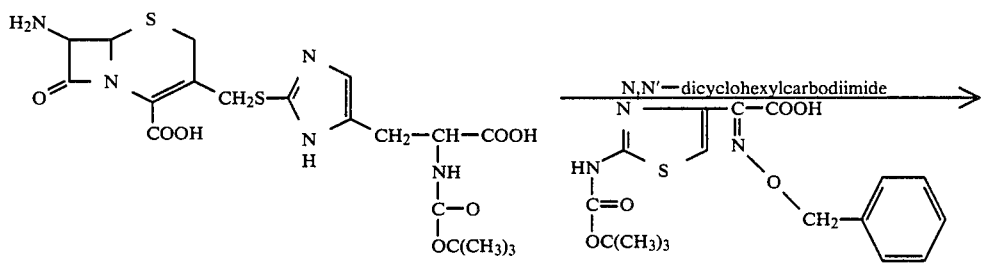

-continued
Reaction Scheme

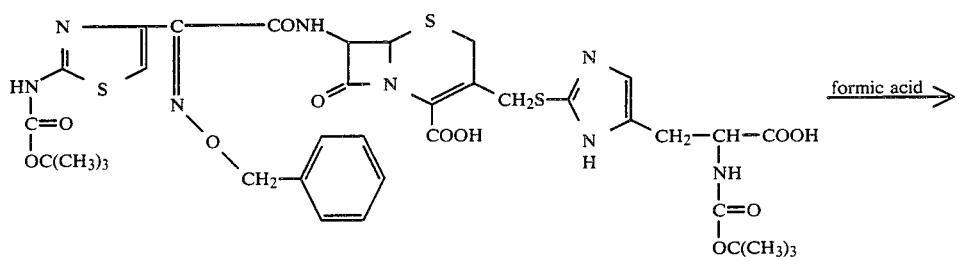

formic acid →

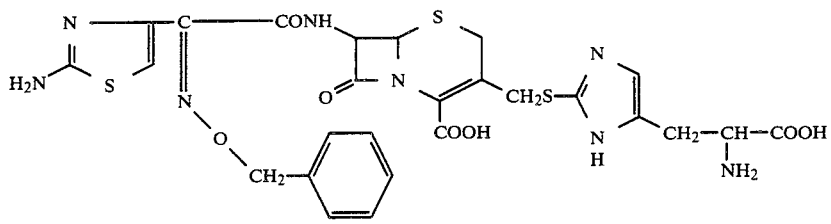

| NMR Spectrum (in DMSO-d₆ and trifluoroacetic acid) | | |
|---|---|---|
| 7.58 ppm | 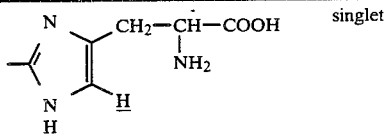 | singlet |
| 7.30 ppm | 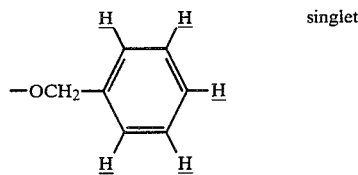 | singlet |
| 7.02 ppm | 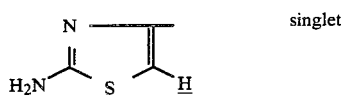 | singlet |
| 5.87 ppm | H-7 | doublet |
| 5.26 ppm | H-6 | doublet |
| 5.13 ppm | —OC$\underline{H}_2$—phenyl | singlet |
| 4.34 ppm | 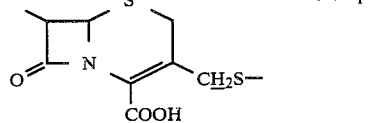 | multiplet |
| 3.79 ppm | 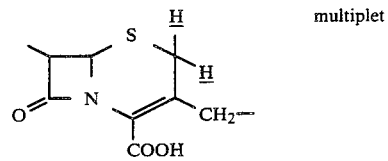 | multiplet |

-continued

| NMR Spectrum (in DMSO-d₆ and trifluoroacetic acid) | | |
|---|---|---|
| 3.31 ppm | 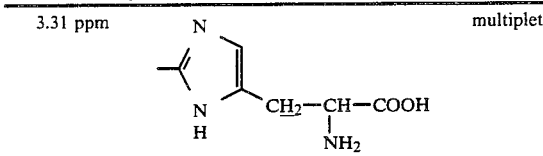 | multiplet |

EXAMPLE 19

Preparation of Compound No. 32

Into 100 ml of water and 60 ml of acetone, 3.0 g of N-tert-butyloxyhistidine, 2.7 g of 7-aminocephalosporanic acid and 1.0 g of sodium iodide were dissolved and 3.0 g of sodium hydrogencarbonate was added and the reaction was carried out at 70° C. for 6 hours in a nitrogen atmosphere, whereby pH of the reaction liquid was controlled to 5.5–6.5. After completion of the reaction, acetone in the reaction liquid was removed by distillation. Isolation by column chromatography using XAD-II gave 3.7 g of the product.

Then, the thus obtained compound was added to 40 ml of tetrahydrofuran and 2.5 moles of a trimethylsilylating agent of bis(trimethylsilyl)acetamide were added thereto. Then 2.8 g of 2-(2-tert-butoxycarbonylamino-4-thiazolyl)-2-(methoxyimino)acetic acid and 1.9 g of N,N'-dicyclohexylcarbodiimide were added to 50 ml of tetrahydrofuran, and the resulting mixture was stirred at 20° C. for 2 hours. Thereafter, the tetrahydrofuran solution obtained by the procedure described above was added to the resulting solution, and the mixture was allowed to react at 20° C. for 10 hours while stirring. Precipitates were separated by filtration. After adding 10 ml of water to the filtrate, water and tetrahydrofuran were removed by distillation under reduced pressure. The residue was dissolved in 50 ml of formic acid, and the reaction was carried out at 10° C. for 2 hours. After removing formic acid by distillation, 20 ml of ether was added. A solid substance precipitated out was taken out and isolated and purified by column chromatography using XAD-II to obtain 2.3 g of the desired product.

It was confirmed by NMR spectra that the product was 7β-[(Z)-2-(2-amino-4-thiazolyl)-2-(methoxyimino)acetamido]-3-[3-(2-amino-2-carboxy)ethyl-1-imidazolyl]methyl-3-cephem-4-carboxylic acid (Compound No. 32).

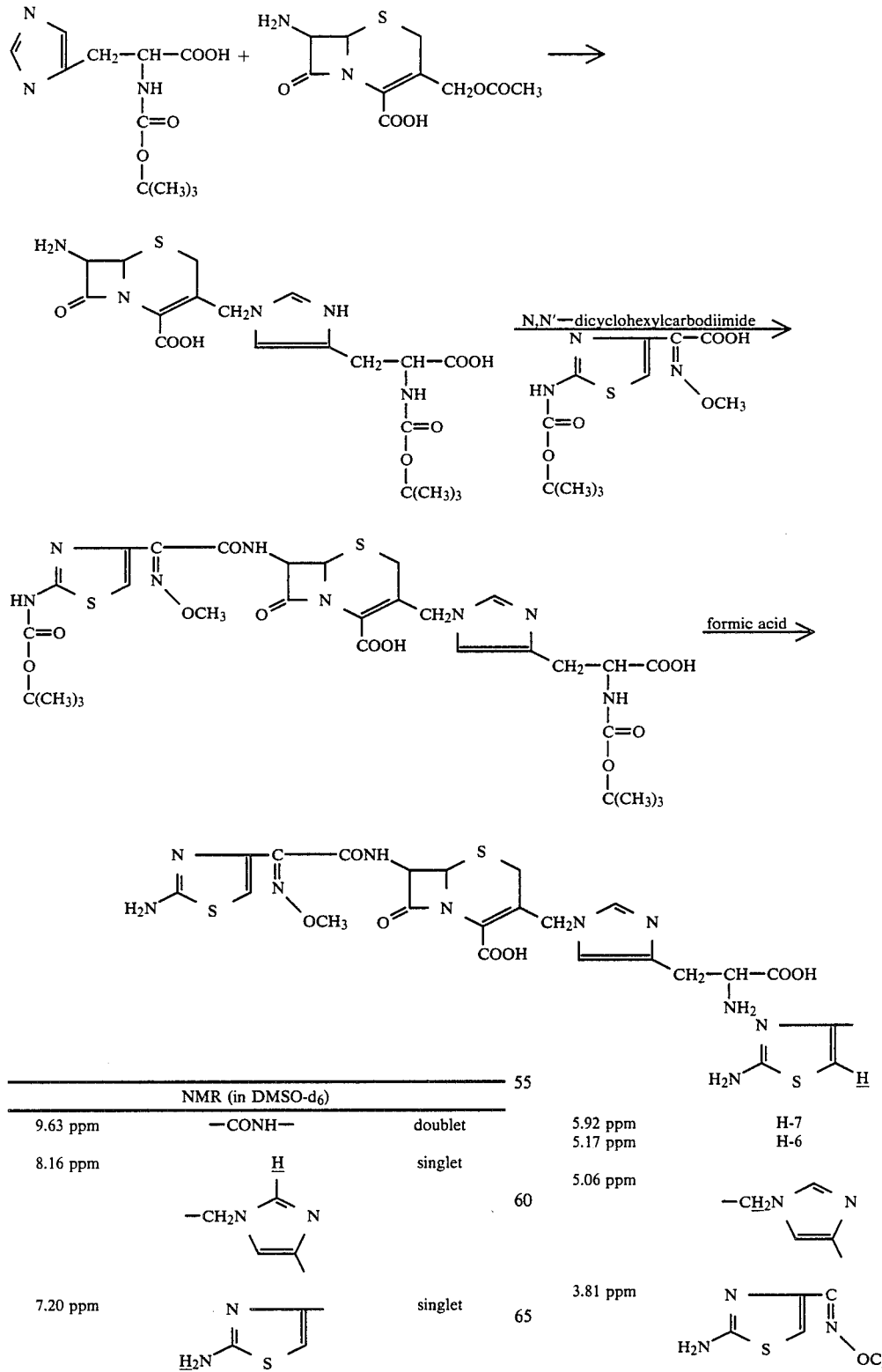

Reaction Scheme

| NMR (in DMSO-d$_6$) | | |
|---|---|---|
| 9.63 ppm | —CONH— | doublet |
| 8.16 ppm | -CH$_2$N imidazolyl H | singlet |
| 7.20 ppm | aminothiazolyl H | singlet |
| 6.75 ppm | | singlet |
| 5.92 ppm | H-7 | multiplet |
| 5.17 ppm | H-6 | doublet |
| 5.06 ppm | —CH$_2$N imidazolyl | singlet |
| 3.81 ppm | OCH$_3$ thiazolyl oxime | singlet |

| NMR (in DMSO-$d_6$) | | |
|---|---|---|
| 3.76 ppm | 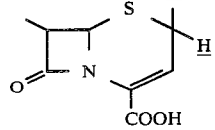 | multiplet |

We claim:
1. A cephalosporin compound represented by the following formula (II) or a physiologically acceptable addition salt thereof:

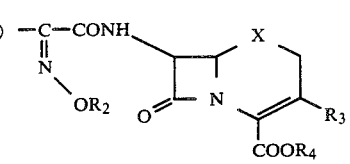  (I)

wherein
$R_1$ represents an amino group or a protected amino group;
Ⓐ represents a 5- or 6-membered heterocyclic ring containing therein 1 to 4 nitrogen, oxygen or sulfur atoms;
$R_2$ represents a normal alkyl group having 1 to 6 carbon atoms, a branched alkyl group having 3 to 6 carbon atoms, an alkoxyalkyl group having 2 to 6 carbon atoms, a cycloalkyl group having 3 to 6 carbon atoms; a cycloalkenyl group having 3 to 6 carbon atoms; a phenyl group; a benzyl group; a 3- to 6-membered heterocyclic ring containing 1 to 4 nitrogen, sulfur or oxygen atoms, or,

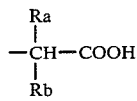

wherein Ra and Rb each, which may be the same or different, represents a hydrogen atom or an alkyl group having 1 to 4 carbon atoms;
$R_3$ represents a compound selected from the group consisting of:

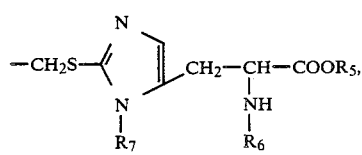

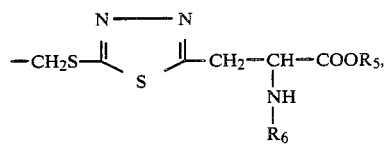

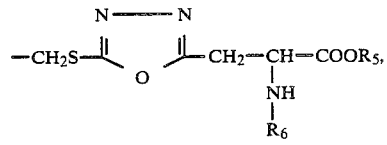

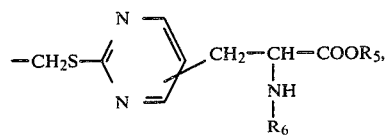

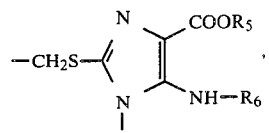

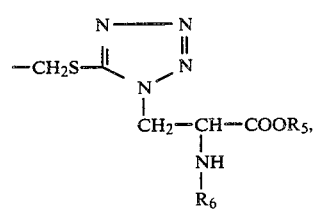

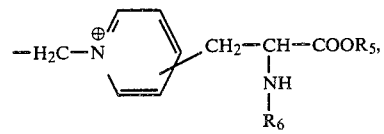

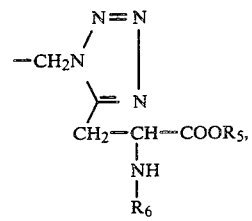

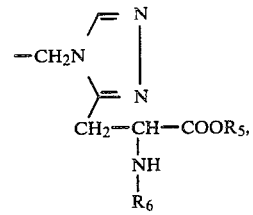

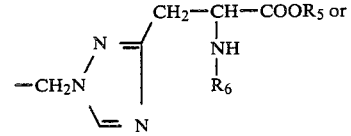

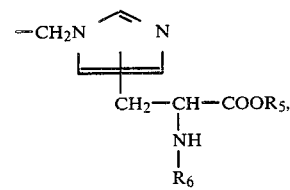

wherein $R_5$ represents a hydrogen atom or a protective group of a carboxyl group; $R_6$ represents a hydrogen atom or a protective group of an amino group; and $R_7$ represents a hydrogen atom or a normal alkyl group having 1 to 6 carbon atoms or a branched alkyl group having 3 to 6 carbon atoms;

X represents a sulfur atom; and $R_4$ represents a hydrogen atom or a protective group of a carboxyl group.

2. The compound as claimed in claim 1 which is selected from the following formulae (II), (III), (IV), (V) and (VI):

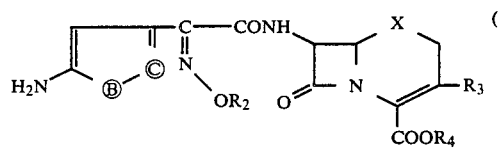
(II)

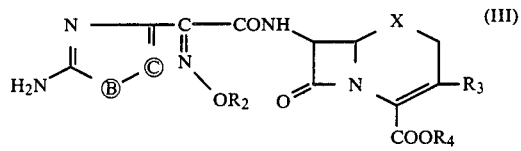
(III)

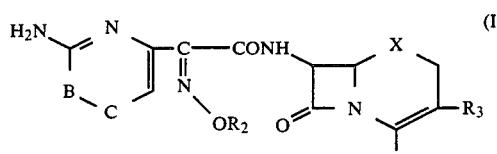
(IV)

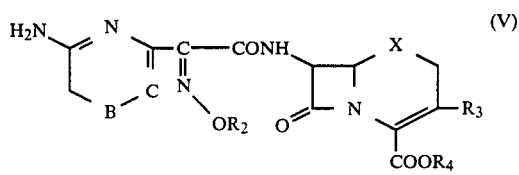
(V)

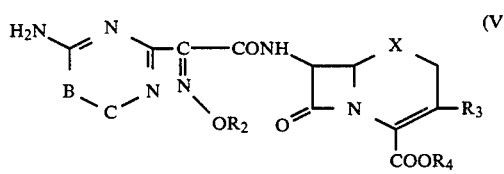
(VI)

wherein Ⓑ represents any one of a sulfur atom, a nitrogen atom and an oxygen atom; Ⓒ represents a carbon atom or a nitrogen atom; and $R_2$, $R_3$, $R_4$ and X represent the same meaning as defined in claim 1.

3. The compound as claimed in claim 2 which is represented by the formula (III)

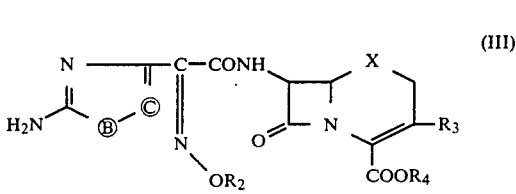
(III)

wherein Ⓑ represents any one of a sulfur atom, a nitrogen atom and an oxygen atom; Ⓒ represents a carbon atom or a nitrogen atom; and each of $R_2$, $R_3$, $R_4$ and X represents the same meaning as defined in claim 1.

4. The compound as claimed in claim 3 which is represented by the formula (VII)

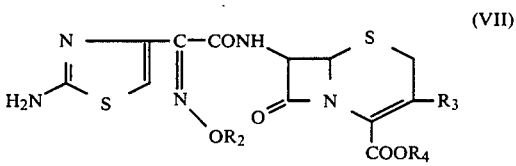
(VII)

wherein each of $R_2$, $R_3$ and $R_4$ represents the same meaning as defined in claim 1.

5. The compound as claimed in claim 2 wherein $R_2$ is a normal alkyl group having 1 to 6 carbon atoms.

6. The compound as claimed in claim 2 wherein $R_2$ is a branched alkyl group having 3 to 6 carbon atoms.

7. The compound as claimed in claim 2 wherein $R_2$ is

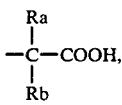

wherein Ra and Rb each, which may be the same or different, represents a hydrogen atom or an alkyl group having 1 to 4 carbon atoms.

8. The cephalosporin compound of claim 1, wherein A is selected from the group consisting of

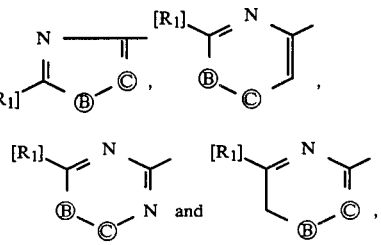

wherein Ⓑ represents any one of —S—, —NH—, —N= and —O—; Ⓒ represents —CH—, —NH— or —N=; and $R_1$ is an amino group or a protective group of amino group.

* * * * *